(12) United States Patent
Stone et al.

(10) Patent No.: US 10,557,691 B2
(45) Date of Patent: Feb. 11, 2020

(54) SELF-REGULATING ELECTROLYTIC GAS GENERATOR AND IMPLANT SYSTEM COMPRISING THE SAME

(71) Applicant: Giner, Inc., Newton, MA (US)

(72) Inventors: Simon G. Stone, Arlington, MA (US); Linda A. Tempelman, Lincoln, MA (US); Melissa Schwenk, Waltham, MA (US)

(73) Assignee: GINER LIFE SCIENCES, INC., Newton, MA (US)

( * ) Notice: Subject to any disclaimer, the term of this patent is extended or adjusted under 35 U.S.C. 154(b) by 33 days.

(21) Appl. No.: 15/814,124

(22) Filed: Nov. 15, 2017

(65) Prior Publication Data

US 2018/0135948 A1    May 17, 2018

Related U.S. Application Data

(60) Provisional application No. 62/422,420, filed on Nov. 15, 2016.

(51) Int. Cl.

| | |
|---|---|
| *F42B 3/04* | (2006.01) |
| *C25B 9/04* | (2006.01) |
| *A61K 48/00* | (2006.01) |
| *A61M 5/142* | (2006.01) |
| *A61M 31/00* | (2006.01) |

(Continued)

(52) U.S. Cl.
CPC ............ *F42B 3/04* (2013.01); *A61K 48/0075* (2013.01); *A61M 5/14276* (2013.01);
(Continued)

(58) Field of Classification Search
None
See application file for complete search history.

(56) References Cited

U.S. PATENT DOCUMENTS

| 150,995 A | 5/1874 | Zwietusch |
|---|---|---|
| 3,005,943 A | 10/1961 | Jaffe |

(Continued)

FOREIGN PATENT DOCUMENTS

| CA | 2112952 A1 | 6/1995 |
|---|---|---|
| CN | 1036511 A | 10/1989 |

(Continued)

OTHER PUBLICATIONS

Tibell et al., "Survival of Macroencapsulated Allogenic Parathyroid Tissue One Year After Transplantation in Nonimmunosuppressed Humans," Cell Transplantation, 10:591-9 (2001).

(Continued)

*Primary Examiner* — Harry D Wilkins, III
(74) *Attorney, Agent, or Firm* — Kriegsman & Kriegsman

(57) ABSTRACT

Self-regulating electrolytic gas generator and implant system including the same. In one embodiment, the electrolytic gas generator is a water electrolyzer and includes a polymer electrolyte membrane with an anode on one side and a cathode on the other side. Anode and cathode seals surround the peripheries of the anode and cathode and include inlets for water and outlets for oxygen and hydrogen, respectively. A cathode current collector is placed in contact with the cathode, and an anode current collector, which may be an elastic, electrically-conductive diaphragm, is positioned proximate to the anode. The anode current collector is reversibly deformable between a first state in which it is in direct physical and electrical contact with the anode and a second state in which it distends, due to gas pressure generated at the anode, so that it is not in physical or electrical contact with the anode, causing electrolysis to cease.

37 Claims, 10 Drawing Sheets

(51) Int. Cl.
  *C25B 9/10* (2006.01)
  *A61M 5/00* (2006.01)
(52) U.S. Cl.
  CPC ............. *A61M 31/002* (2013.01); *C25B 9/04* (2013.01); *A61M 2005/006* (2013.01); *A61M 2005/14204* (2013.01); *A61M 2202/0208* (2013.01); *A61M 2205/7536* (2013.01); *C25B 9/10* (2013.01)

(56) References Cited

U.S. PATENT DOCUMENTS

| | | | |
|---|---|---|---|
| 3,282,875 A | 11/1966 | Connolly et al. | |
| 3,373,057 A | 3/1968 | Jost et al. | |
| 3,453,086 A | 7/1969 | Harm | |
| 3,783,868 A | 1/1974 | Bokros | |
| 3,933,526 A | 1/1976 | Rackin | |
| 4,057,479 A | 11/1977 | Campbell | |
| 4,193,860 A * | 3/1980 | Folser | C04B 35/532 204/284 |
| 4,212,714 A * | 7/1980 | Coker | C25B 1/46 204/263 |
| 4,214,958 A | 7/1980 | Coker et al. | |
| 4,233,146 A * | 11/1980 | Rothmayer | B01D 61/30 204/255 |
| 4,341,604 A * | 7/1982 | DeNora | C25B 1/24 205/525 |
| 4,343,690 A * | 8/1982 | de Nora | C25B 1/46 204/263 |
| 4,470,889 A | 9/1984 | Ezzell et al. | |
| 4,478,695 A | 10/1984 | Ezzell et al. | |
| 4,510,473 A | 4/1985 | Schweiger et al. | |
| 4,520,254 A | 5/1985 | Steiger et al. | |
| 4,539,539 A | 9/1985 | Schweiger et al. | |
| 5,011,472 A | 4/1991 | Aebischer et al. | |
| 5,026,615 A | 6/1991 | Tucholski | |
| 5,338,662 A | 8/1994 | Sadri | |
| 5,356,771 A | 10/1994 | O'Dell | |
| 5,362,622 A | 11/1994 | O'Dell et al. | |
| 5,385,821 A | 1/1995 | O'Dell et al. | |
| 5,586,438 A | 12/1996 | Fahy | |
| 5,788,682 A | 8/1998 | Maget | |
| 5,951,538 A | 9/1999 | Joshi et al. | |
| 5,965,433 A | 10/1999 | Gardetto et al. | |
| 6,060,640 A | 5/2000 | Pauley et al. | |
| 6,171,368 B1 | 1/2001 | Maget et al. | |
| D453,828 S | 2/2002 | Brassil et al. | |
| 6,368,592 B1 * | 4/2002 | Colton | A61K 33/00 424/423 |
| 6,475,716 B1 | 11/2002 | Seki | |
| 6,492,103 B1 | 12/2002 | Taylor | |
| 6,492,431 B1 | 12/2002 | Cisar | |
| 6,673,594 B1 | 1/2004 | Owen et al. | |
| 6,677,150 B2 | 1/2004 | Alford et al. | |
| 6,773,458 B1 | 8/2004 | Brauker et al. | |
| 6,811,905 B1 | 11/2004 | Cropley et al. | |
| 6,824,915 B1 | 11/2004 | Pedicini | |
| 6,852,441 B2 | 2/2005 | Milgate, Jr. et al. | |
| 6,977,140 B1 | 12/2005 | Owen et al. | |
| 6,994,954 B2 | 2/2006 | Taylor | |
| 7,176,015 B2 | 2/2007 | Alford et al. | |
| 7,316,857 B1 * | 1/2008 | Swanson | C25B 1/00 204/271 |
| 7,572,622 B2 | 8/2009 | Hassanein et al. | |
| 7,651,835 B2 | 1/2010 | Hassanein et al. | |
| 7,892,222 B2 | 2/2011 | Vardi et al. | |
| 7,947,094 B2 | 5/2011 | Fiebig | |
| 7,947,405 B2 | 5/2011 | Mittelsteadt et al. | |
| 8,012,500 B2 | 9/2011 | Rotem et al. | |
| 8,043,271 B2 | 10/2011 | Stern et al. | |
| 8,083,821 B2 | 12/2011 | Tempelman et al. | |
| 8,100,672 B2 | 1/2012 | Walavalkar et al. | |
| 8,349,151 B2 | 1/2013 | Schmitt et al. | |
| 8,647,393 B2 | 2/2014 | Marshall et al. | |
| 8,784,389 B2 | 7/2014 | Stern et al. | |
| 8,900,763 B2 | 12/2014 | Lundblad et al. | |
| 9,357,764 B2 | 6/2016 | Tempelman et al. | |
| 9,433,557 B2 | 9/2016 | Green et al. | |
| 9,595,727 B2 | 3/2017 | Mittelsteadt et al. | |
| 10,266,808 B2 | 4/2019 | Kelly et al. | |
| 10,272,179 B2 | 4/2019 | Martinson et al. | |
| 2001/0013469 A1 * | 8/2001 | Shiepe | C25B 1/12 204/252 |
| 2002/0033333 A1 | 3/2002 | Riecke | |
| 2003/0008192 A1 | 1/2003 | Freund et al. | |
| 2003/0087427 A1 | 5/2003 | Colton et al. | |
| 2004/0058432 A1 | 3/2004 | Owen et al. | |
| 2005/0074657 A1 | 4/2005 | Rusta-Sallehy et al. | |
| 2005/0136092 A1 | 6/2005 | Rotem et al. | |
| 2005/0221269 A1 | 10/2005 | Taylor et al. | |
| 2006/0160204 A1 | 7/2006 | Hassanein et al. | |
| 2006/0292544 A1 | 12/2006 | Hassanein et al. | |
| 2008/0187901 A1 | 8/2008 | Doorschodt et al. | |
| 2008/0226750 A1 | 9/2008 | Roth et al. | |
| 2008/0248350 A1 | 10/2008 | Little et al. | |
| 2009/0012502 A1 | 1/2009 | Rotem et al. | |
| 2009/0042072 A1 | 2/2009 | Vu et al. | |
| 2009/0112170 A1 | 4/2009 | Wells et al. | |
| 2009/0197240 A1 | 8/2009 | Fishman et al. | |
| 2010/0108534 A1 | 5/2010 | Carlstrom, Jr. et al. | |
| 2010/0130916 A1 | 5/2010 | Stern et al. | |
| 2010/0196439 A1 | 8/2010 | Beck et al. | |
| 2010/0204683 A1 | 8/2010 | Bodor et al. | |
| 2010/0243434 A1 * | 9/2010 | Maget | A01M 1/2055 204/230.5 |
| 2010/0330547 A1 | 12/2010 | Tempelman et al. | |
| 2011/0008886 A1 | 1/2011 | Hering et al. | |
| 2011/0054387 A1 | 3/2011 | Stern et al. | |
| 2011/0212431 A1 | 9/2011 | Bunegin et al. | |
| 2011/0295241 A1 | 12/2011 | Ziaie et al. | |
| 2012/0209434 A1 * | 8/2012 | Kurashina | C25B 1/12 700/273 |
| 2013/0040223 A1 | 2/2013 | Tsukamoto et al. | |
| 2013/0264218 A1 * | 10/2013 | Vinton | C01B 5/00 205/628 |
| 2014/0257515 A1 | 9/2014 | So et al. | |
| 2015/0112247 A1 * | 4/2015 | Tempelman | A61F 2/022 604/26 |
| 2018/0133383 A1 | 5/2018 | Ferrante et al. | |
| 2019/0119462 A1 | 4/2019 | Desai et al. | |
| 2019/0125668 A1 | 5/2019 | Fox et al. | |
| 2019/0125937 A1 | 5/2019 | Rotem | |

FOREIGN PATENT DOCUMENTS

| | | |
|---|---|---|
| CN | 101569559 A | 11/2009 |
| EP | 0470726 A1 | 2/1992 |
| JP | H07196401 A | 8/1995 |
| JP | 2008519830 A | 6/2008 |
| WO | 0121234 A1 | 3/2001 |
| WO | 0150983 A1 | 7/2001 |
| WO | 2006112720 A2 | 10/2006 |
| WO | 2006122169 A2 | 11/2006 |
| WO | 2008079997 A2 | 7/2008 |
| WO | 2009031154 A2 | 3/2009 |
| WO | 2009094236 A2 | 7/2009 |
| WO | 2010049996 A1 | 5/2010 |
| WO | 2011159246 A1 | 12/2011 |
| WO | 2015048184 A1 | 4/2015 |
| WO | 2018085714 A1 | 5/2018 |
| WO | 2018102077 A2 | 6/2018 |
| WO | 2018144098 A1 | 8/2018 |
| WO | 2018144099 A1 | 8/2018 |
| WO | 2019067766 A1 | 4/2019 |
| WO | 2019089943 A1 | 5/2019 |

OTHER PUBLICATIONS

Pedraza et al., "Preventing hypoxia-induced cell death in beta cells and islets via hydrolytically activated, oxygen-generating biomaterials," PNAS, 109(11):4245-4250 (2012).

(56) References Cited

OTHER PUBLICATIONS

Ludwig et al., "Improvement of islet function in a bioartificial pancreas by enhanced oxygen supply and growth hormone releasing hormone agonist," PNAS, 109(13):5022-5027 (2012).
Tarantal et al., "Real-time Bioluminescence Imaging of Macroencapsulated Fibroblasts Reveals Allograft Protection in Rhesus Monkeys (Macaca mulatta)," Transplantation, 88(1):38-41 (2009).
Colton, "Oxygen supply to encapsulated therapeutic cells," Advanced Drug Delivery Reviews, 67-68:93-110 (Feb. 27, 2014).
Weir, "Islet encapsulation: advances and obstacles," Diabetologia, 56:1458-1461 (Apr. 30, 2013).
Ludwig et al., "Transplantation of human islets without immunosuppression," PNAS, 110(47):19054-19058 (Nov. 19, 2013).
Ohsawa et al., "Hydrogen acts as a therapeutic antioxidant by selectively reducing cytotoxic oxygen radicals," Nature Medicine, 13(6):688-694 (2007).
Burns et al., "The Survival of Mammalian Tissues Perfused with Intravascular Gas Mixtures of Oxygen and Carbon Dioxide," Can. J. Biochem. Physiol., 36:499-504 (1958).
Neufeld et al., "The Efficacy of an Immunoisolating Membrane System for Islet Xenotransplantation in Minipigs," PLoS One, 8(8):e70150 (pp. 1-13) (Aug. 1, 2013).
Wood et al., "The hydrogen highway to reperfusion therapy," Nature Medicine, 13(6):673-674 (2007).
Saad et al., "Extension of Ischemic Tolerance of Porcine Livers by Cold Preservation Including Postconditioning with Gaseous Oxygen," Transplantation, 71:498-502 (2001).
Kin et al., "Islet Isolation and Transplantation Outcomes of Pancreas Preserved with University of Wisconsin Solution Versus Two-Layer Method Using Preoxygenated Perfluorocarbon," Transplantation, 82(10):1286-1290 (2006).
Sudan et al., "A New Technique for Combined Liver/Small Intestinal Transplantation," Transplantation, 72 (11):1846-1848 (2001).
Kuhn-Regnier et al., "Coronary oxygen persufflation combined with HTK cardioplegia prolongs the preservation time in heart transplantation," European Journal of Cardio-thoracic Surgery, 17:71-76 (2000).
Hunt et al., "Cannulation of the portal vein for cytotoxic liver perfusion in colorectal carcinomas: an alternative approach," Annals of the Royal College of Surgeons of England, 68:36-38 (1986).
Wu et al., "In Situ Electrochemical Oxygen Generation with an Immunoisolation Device," Ann. N.Y. Acad. Sci., pp. 105-125 (1999).
Moers et al., "Machine Perfusion or Cold Storage in Deceased-Donor Kidney Transplantation," N. Eng. J. Med., 360:7-19 (2009).
Emamaullee et al., "Caspase Inhibitor Therapy Synergizes With Costimulation Blockade to Promote Indefinite Islet Allograft Survival," Diabetes, 59:1469-77 (2010).
Emamaullee et al., "The Caspase Selective Inhibitor EP1013 Augments Human Islet Graft Function and Longevity in Marginal Mass Islet Transplantation in Mice," Diabetes, 57:1556-66 (2008).
Expanding Transplantation Possibilities, Lifeline Scientific Annual Report 2010, Lifeline Scientific, Inc., Itasca, Illinois.
Calhoon et al., "Twelve-Hour Canine Heart Preservation With a Simple, Portable Hypothermic Organ Perfusion Device," Ann. Thorac. Surg., 62:91-3 (1996).
Hassanein et al., "Continuous Perfusion of Donor Hearts in the Beating State Extends Preservation Time and Improves Recovery of Function," J. Thorac. Cardiovasc. Surg., 116:821-30 (1998).
Weegman et al., "Continuous Real-Time Viability Assessment of Kidneys Based on Oxygen Consumption," Transplant Proc., 42(6):2020-2023 (2010).doi:10.1016/j.transproceed.2010.05.082.
Suszynski et al., "Persufflation (or gaseous oxygen perfusion) as a method of organ preservation," Cryobiology, 64 (3):125-143 (2012).
Scott et al., "Pancreas Oxygen Persufflation Increases ATP Levels as Shown by Nuclear Magnetic Resonance," Transplantation Proceedings, 42(6): 2011-2015 (Jul.-Aug. 2010).
Fischer, "Methods of Cardiac Oxygen Persufflation," Methods in Bioengineering: Organ Preservation and Reengineering, editors Korkut Uygun and Charles Y. Lee, published by Artech House, Norwood, MA (2011).
Treckmann et al., "Retrograde Oxygen Persufflation Preservation of Human Livers: A Pilot Study," Liver Transplantation, 14:358-64 (2008).
Koetting et al., "Optimal Time for Hypothermic Reconditioning of Liver Grafts by Venous Systemic Oxygen Persufflation in a Large Animal Model," Transplantation, 91(1):42-7 (2011).
Guibert et al., "Organ Preservation: Current Concepts and New Strategies for the Next Decade," Transfusion Medicine and Hemotherapy, 38:125-142 (2011).
Caballero-Corbalan et al., "No Beneficial Effect of Two-Layer Storage Compared with UW-Storage on Human Islet Isolation and Transplantation," 84(7):864-9 (2007).
Minor et al., "Energetic recovery in porcine grafts by minimally invasive liver oxygenation," Journal of Surgical Research, published online Mar. 14, 2012.
Taylor et al., "Current state of hypothermic machine perfusion preservation of organs: The clinical perspective," Cryobiology (2009), doi:10.1016/j.cryobiol.2009.10.006.
Scott et al., "Persufflation Improves Pancreas Preservation When Compared With the Two-Layer Method," Transplantation Proceedings, 42(6): 2016-2019 (Jul.-Aug. 2010).
J.H. Fischer: Methods of Cardiac Oxygen Persufflation. Author manuscript available at ResearchGate.net Mar. 15, 2018. Published in final edited form as: Methods of Bioengineering: Organ preservation and reengineering. Eds. Korkut Uygun and Charles Y. Lee. Artech House Boston, London 2011, p. 105-126. ISBN: 13: 978-1-60807-013-8.
Avgoustiniatos et al., "Effect of External Oxygen Mass Transfer Resistances on Viability of Immunoisolated Tissue," Ann NY Acad Sci, 831:145-167 (1997).
Barkai et al., "Enhanced Oxygen Supply Improves Islet Viability in a New Bioartificial Pancreas," Cell Transplantation, 22:1463-1476 (2013).
Bellin et al., "Potent induction immunotherapy promotes long-term insulin independence after islet transplantation in type 1 diabetes," Am J Transplant., 12(6):1576-1583 (2012).
Bergenstal et al., "Effectiveness of Sensor-Augmented Insulin-Pump Therapy in Type 1 Diabetes," N Eng J Med, 363 (4):311-320 (2010).
Goh et al.' "Dual Perfluorocarbon Method to Noninvasively Monitor Dissolved Oxygen Concentration in Tissue Engineered Constructs, in vitro and in vivo," Biotechnol. Prog., 27:1115-1125 (2011).
Goh et al., "In Vivo Noninvasive Monitoring of Dissolved Oxygen Concentration Within an Implanted Tissue-Engineered Pancreatic Construct," Tissue Engineering: Part C, 17(9):887-894 (2011).
Klonoff et al., "Innovations in Technology for the Treatment of Diabetes: Clinical Development of the Artificial Pancreas (an Autonomous System)," Journal of Diabetes Science and Technology, 5(3):804-826 (2011).
Ludwig et al., "A Novel Device for Islet Transplantation Providing Immune Protection and Oxygen Supply," Horm Metab Res, 42:918-922 (2010).
Luo et al., Recovery of Neurological Functions in Non-Human Primate Model of Parkinson's Disease by Transplantation of Encapsulated Neonatal Porcine Choroid Plexus Cells, Journal of Parkinson's Disease, 3: 275-291 (2013).
O'Sullivan et al., "Islets Transplanted in Immunoisolation Devices: A Review of the Progress and the Challenges that Remain," Endocrine Reviews, 32(6):827-844 (2011).
Ritz-Laser et al., "Molecular Detection of Circulating Beta-Cells After Islet Transplantation," Diabetes, 51:557-561 (2002).
Storrs et al., "Preclinical Development of the Islet Sheet," Ann NY Acad Sci, 944:252-266 (2001).
Wang et al., "Donor Treatment With Carbon Monoxide Can Yield Islet Allograft Survival and Tolerance," Diabetes, 54:1400-1406 (2005).
International Search Report dated Feb. 12, 2018, in PCT Application No. PCT/US17/61859, the corresponding PCT application to the present application.
Written Opinion dated Feb. 12, 2018, in PCT Application No. PCT/US17/61859, the corresponding PCT application to the present application.

(56) References Cited

OTHER PUBLICATIONS

"Gore Technologies" (Gore) Nov. 12, 2016 (Dec. 11, 2016) [online] retrieved from <URL:https://web.archive.org/web/20161112003850/https://www.gore.com/about/technologies>.

Zeman et al., "Evaluation of Oxygen Permeability of Polyethylene Films," Technical Sciences, 15(2): 331-345 (2012).

International Preliminary Report on Patentability dated May 21, 2019, in PCT Application No. PCT/US2017/061859, the corresponding PCT application to the present application.

Abstract of Kanehashi et al., "Gas and Vapor Transport in Membranes," Membrane Characterization, 309-336 (2017).

U.S. Appl. No. 16/415,977, inventors Melissa N. Schwenk et al., filed May 17, 2019.

PCT Application No. PCT/US19/32990, inventors Melissa N. Schwenk et al., filed May 17, 2019.

\* cited by examiner

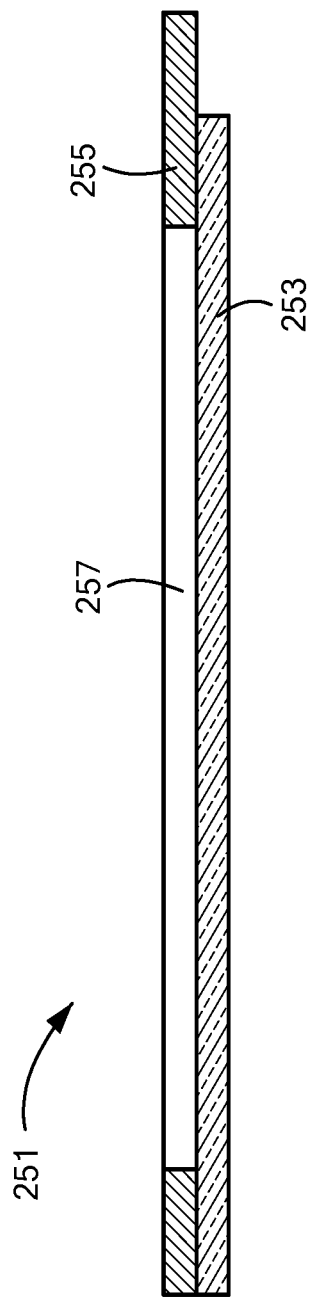
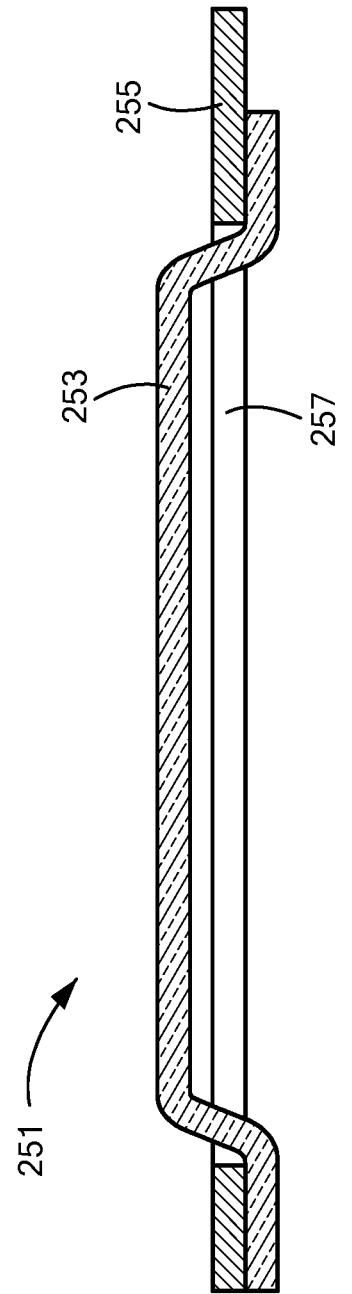

SELF-REGULATING ELECTROLYTIC GAS GENERATOR AND IMPLANT SYSTEM COMPRISING THE SAME

CROSS-REFERENCE TO RELATED APPLICATIONS

The present application claims the benefit under 35 U.S.C. 119(e) of U.S. Provisional Patent Application No. 62/422,420, inventors Simon G. Stone et al., filed Nov. 15, 2016, the disclosure of which is incorporated herein by reference.

FEDERALLY SPONSORED RESEARCH OR DEVELOPMENT

This invention was made with government support under Grant Number 1R43DK113536-01, awarded by NIH-NIDDK. The government has certain rights in the invention.

BACKGROUND OF THE INVENTION

The present invention relates generally to electrolytic gas generators and relates more particularly to a novel electrolytic gas generator and to an implant system comprising the same.

The controlled generation of one or more types of gases at point-of-use is of significance to a multitude of industrial and medical applications. Electrolysis is a common technique for generating such gases and typically involves converting a feedstock (which is often a low cost, stable reactant) to a useful commodity (which is often a high cost or unstable product) using an electrical current. Electrolysis is favored as a production technique due to its high process efficiency, its product selectivity, and its inherent ability to control production rate by controlling the applied current. Devices designed to generate one or more gases using electrolysis are sometimes referred to as electrolytic gas generators. Electrolytic gas generators for hydrogen production, for instance, are used frequently in analytical laboratories to supply high purity hydrogen, on-demand, for use as carrier and detector gases in gas chromatographs. Electrolytic gas generators for oxygen production, for example, have been used to generate oxygen in situ at skin wounds to improve the healing process for severe burns and diabetic ulcers. Such electrolytic gas generators typically require several basic system components to govern performance and safety, and these basic system components generally include current control (e.g., a DC power supply for maintaining generation rate and voltage efficiency), downstream pressure and gas purity monitoring (e.g., for process and environmental safety), and fluid management (e.g., water reactant feed pump and gas-liquid separation units). However, as can be appreciated, such components can increase the size, cost, and complexity of the overall system and can make the overall system more difficult to maintain. Also, although hydrogen and oxygen are two of the more common gases produced by electrolytic gas generators, electrolytic gas generators can be used to produce other gases, such as, but not limited to, carbon dioxide, chlorine, ozone, hydrogen peroxide, chlorine dioxide, nitric oxide, sulfur dioxide, hydrogen sulfide, carbon monoxide, ammonia, hydrogen chloride, hydrogen bromide, and hydrogen cyanide.

An emerging medical application for in situ gas generation is in the provision of gaseous oxygen to cells and/or tissues that are located under the skin or that are included as part of a subdermal implant device. Subdermal implant devices are useful implements for the in situ generation and dissemination of therapeutics to a patient in need thereof for the treatment of various diseases, disorders, and/or conditions. Typically, such implant devices comprise cells and/or tissues that are encapsulated within a suitable implantable container. The implantable container is typically designed to allow the cells and/or tissues to produce the desired therapeutic and for the dissemination of the produced therapeutic to the patient while, at the same time, limiting an immunological response. As can be appreciated, the delivery of essential gases (e.g., oxygen) and nutrients to implant devices is important for the viability and function of the cells and/or tissues contained therein. Regarding the delivery of gases to the implant device, it is especially important to the safety of the patient that excessive gas pressures be prevented and/or mitigated so as to obviate the risk of pain, infection, tissue damage, or embolism in the patient.

In U.S. Patent Application Publication No. US 2015/0112247 A1, inventors Tempelman et al., which was published Apr. 23, 2015, and which is incorporated herein by reference in its entirety, there is disclosed a system for gas treatment of a cell implant. According to the aforementioned publication (hereinafter "the '247 publication"), the system enhances the viability and function of cellular implants, particularly those with high cellular density, for use in human or veterinary medicine. The system utilizes a miniaturized electrochemical gas generator subsystem that continuously supplies oxygen and/or hydrogen to cells within an implantable and immunoisolated cell containment subsystem to facilitate cell viability and function at high cellular density while minimizing overall implant size. The cell containment subsystem is equipped with features to allow gas delivery through porous tubing or gas-only permeable internal gas compartments within the implantable cell containment subsystem. Furthermore, the gas generator subsystem includes components that allow access to water for electrolysis while implanted, thereby promoting long-term implantability of the gas generator subsystem. An application of the system is a pancreatic islet (or pancreatic islet analogue) implant for treatment of Type I diabetes (T1D) that would be considered a bio-artificial pancreas.

In U.S. Pat. No. 7,892,222 B2, inventors Vardi et al., which issued Feb. 22, 2011, and which is incorporated herein by reference in its entirety, there is disclosed an implantable device comprising a chamber for holding functional cells and an oxygen generator for providing oxygen to the cells within the chamber. According to the aforementioned patent (hereinafter "the '222 patent"), functional cells are loaded into the chamber of the device that is then implanted in the body. The device comprises an oxygen generator, i.e., an element that can produce oxygen and make it available to the functional cells, so that the functional cells do not suffer from hypoxia. The oxygen generator thus produces oxygen and typically releases the oxygen in the cell's vicinity. In one embodiment, the oxygen generator comprises a pair of electrodes. When an electric potential is applied across the electrodes, oxygen is released by electrolysis of ambient water molecules present within the chamber. The electrodes are connected to a power source, typically a rechargeable battery. The chamber may further comprise an oxygen sensor that determines the oxygen concentration in the vicinity of the functional cells. A microprocessor may be provided to turn on the oxygen generator when the sensor detects that the oxygen concentration is below a predetermined minimum and to turn it off when the oxygen concentration is above a predetermined maximum.

In U.S. Pat. No. 6,368,592 B1, inventors Colton et al., which issued Apr. 9, 2002, and which is incorporated herein by reference in its entirety, there is disclosed a method of delivering oxygen to cells by electrolyzing water. According to the aforementioned patent (hereinafter "the '592 patent"), oxygen is supplied to cells in vitro or in vivo by generating oxygen with an oxygen generator that electrolyzes water to oxygen and hydrogen. Oxygen can be generated substantially without generating free hydrogen using a multilayer electrolyzer sheet having a proton exchange membrane sandwiched by an anode layer and a cathode layer. The oxygen generator may be used to supply oxygen to cells contained by a culture plate, a culture flask, a microtiter plate or an extracorporeal circuit, or to cells in an encapsulating chamber for implanting in the body such as an immunoisolation chamber bounded by a semipermeable barrier layer that allows selected components to enter and leave the chamber. A bioactive molecule may be present with the cells. Oxygen can be delivered in situ to cells within the body such as by implanting the oxygen generator in proximity to cell-containing microcapsules in an intraperitoneal space, or by implanting a system containing the oxygen generator in proximity to an immunoisolation chamber containing cells. The oxygen generator may be connected to a current control circuit and a power supply.

One shortcoming that has been identified by the present inventors with electrolytic gas generators of the type conventionally used with subdermal implant devices is that such electrolytic gas generators either are configured to continuously generate a gas (which, in most cases, is oxygen) or are equipped with some external mechanism, such as a gas sensor and a current control device, to control actuation of the electrolytic gas generator. However, the continuous generation of gas may be undesirable for a subdermal implant device, especially if the rate of gas generation exceeds the rate at which the generated gas is consumed by cells and/or tissues of the implant device, as excess gas can lead to damage to the implant and/or the patient. On the other hand, external mechanisms for controlling gas generation can increase the size of the implant, which is undesirable, as well as adding to the cost and complexity of the implant.

SUMMARY OF THE INVENTION

It is an object of the present invention to provide a novel electrolytic gas generator.

It is another object of the present invention to provide an electrolytic gas generator as described above that addresses at least some of the shortcomings associated with existing electrolytic gas generators.

It is still another object of the present invention to provide an electrolytic gas generator as described above that is compact, has a minimal number of parts, is inexpensive to manufacture, and is easy to operate.

Therefore, according to one aspect of the invention, there is provided an electrolytic gas generator for electrolyzing a reactant to generate at least a first gas, the electrolytic gas generator comprising (a) a polymer electrolyte membrane, the polymer electrolyte membrane having opposing first and second faces; (b) a first electrode, the first electrode being electrically coupled to the first face of the polymer electrolyte membrane; (c) a second electrode, the second electrode being electrically coupled to the second face of the polymer electrolyte membrane; (d) a first current collector, the first current collector being electrically-conductive and being reversibly deformable between a first state in which the first current collector is electrically coupled to the first electrode and a second state in which the first current collector is at least partially electrically disconnected from the first electrode; (e) a second current collector, the second current collector being electrically-conductive and being electrically coupled to the second electrode; and (f) a power source, the power source being electrically coupled to the first current collector and to the second current collector; (g) whereby, when the first current collector is in the first state and the reactant is supplied to the electrolytic gas generator, a first gas is generated at the interface of the first electrode and the polymer electrolyte membrane.

In a more detailed feature of the invention, the electrolytic gas generator may be a water electrolyzer.

In a more detailed feature of the invention, the first current collector may be in direct physical and electrical contact with the first electrode in the first state and may be completely physically and electrically disconnected from the first electrode in the second state.

In a more detailed feature of the invention, the first current collector may be in direct physical and electrical contact with the first electrode in the first state and may be partially physically and electrically disconnected from the first electrode in the second state.

In a more detailed feature of the invention, the first electrode may be an anode, and the second electrode may be a cathode.

In a more detailed feature of the invention, the electrolytic gas generator may further comprise a resiliently-compressible member engaged with the first current collector to bias the first current collector towards the first state.

In a more detailed feature of the invention, the resiliently-compressible member may comprise a block of foam.

In a more detailed feature of the invention, the foam may be an open-cell foam.

In a more detailed feature of the invention, the foam may be a closed-cell foam.

In a more detailed feature of the invention, the first current collector may be elastic.

In a more detailed feature of the invention, the first current collector may comprise a non-porous, gas-impermeable, electrically-conductive diaphragm.

In a more detailed feature of the invention, the first current collector may comprise a non-porous, gas-permeable, electrically-conductive diaphragm.

In a more detailed feature of the invention, the first current collector may comprise an electrically-conductive diaphragm and a ring terminal.

In a more detailed feature of the invention, the second current collector may comprise at least one pore.

In a more detailed feature of the invention, the electrolytic gas generator may further comprise a first fluid inlet for admitting outside fluid into the electrolytic gas generator to be electrolyzed.

In a more detailed feature of the invention, the electrolytic gas generator may further comprise a first fluid outlet for discharging from the electrolytic gas generator a first gas generated thereby.

According to another aspect of the invention, there is provided an electrolytic gas generator for electrolyzing water to generate oxygen and hydrogen gases, the electrolytic gas generator comprising (a) a polymer electrolyte membrane, the polymer electrolyte membrane having opposing first and second faces; (b) a first electrode, the first electrode being electrically coupled to the first face of the polymer electrolyte membrane; (c) a second electrode, the second electrode being electrically coupled to the second face of the polymer electrolyte membrane; (d) a first current collector, the first current collector being electrically-conductive and being reversibly deformable, when subjected to gas pressure, between a first state in which the first current collector is electrically coupled to the first electrode and a second state in which the first current collector is at least partially electrically disconnected from the first electrode; (e) a second current collector, the second current collector being electrically-conductive and being electrically coupled to the second electrode; (f) a first seal, the first seal being disposed around a periphery of the first electrode, the first seal comprising a fluid outlet for discharging one of hydrogen and oxygen generated at the first electrode; (g) a second seal, the second seal being disposed around a periphery of the second electrode, the second seal comprising a fluid outlet for discharging the other of hydrogen and oxygen generated at the second electrode; (h) a first endplate, the first current collector being positioned between the first endplate and the polymer electrolyte membrane; (i) a second endplate, the second current collector being positioned between the second endplate and the polymer electrolyte membrane; (j) wherein at least one of the first seal, the second seal, the first endplate and the second endplate has at least one inlet for admitting outside water; and (k) a power source, the power source being electrically coupled to the first current collector and to the second current collector; (l) whereby, when the first current collector is in the first state and water is supplied to the electrolytic gas generator, one of hydrogen and oxygen gas is generated at the interface of the first electrode and the polymer electrolyte membrane and the other of hydrogen and oxygen is generated at the interface of the second electrode and the polymer electrolyte membrane.

In a more detailed feature of the invention, the first current collector may be in direct physical and electrical contact with the first electrode in the first state and may be completely physically and electrically disconnected from the first electrode in the second state.

In a more detailed feature of the invention, the first current collector may be in direct physical and electrical contact with the first electrode in the first state and may be partially physically and electrically disconnected from the first electrode in the second state.

In a more detailed feature of the invention, the first electrode may be an anode, and the second electrode may be a cathode.

In a more detailed feature of the invention, the electrolytic gas generator may further comprise a resiliently-compressible member positioned between and engaged with the first endplate and the first current collector to bias the first current collector towards the first state.

In a more detailed feature of the invention, the resiliently-compressible member may comprise a block of foam.

In a more detailed feature of the invention, the first current collector may comprise an elastic, non-porous, gas-impermeable, electrically-conductive diaphragm.

In a more detailed feature of the invention, the first current collector may comprise an elastic, non-porous, gas-permeable, electrically-conductive diaphragm, the foam may be an open-cell foam, and the first endplate may comprise at least one pore.

In a more detailed feature of the invention, the electrolytic gas generator may further comprise an ultrafiltration membrane positioned within the at least one pore of the first endplate.

In a more detailed feature of the invention, the second current collector may comprise at least one pore, and the second endplate may comprise at least one pore.

In a more detailed feature of the invention, the electrolytic gas generator may further comprise a liquid-permeable, gas-impermeable interface layer positioned between the second current collector and the second endplate.

In a more detailed feature of the invention, at least one of the first seal and the second seal has a fluid inlet for admitting outside water.

It is another object of the present invention to provide an implant system comprising the above-described electrolytic gas generator.

Therefore, according to one aspect of the invention, there is provided an implant system, the implant system comprising (a) at least one of the types of electrolytic gas generators described above; (b) a container for holding implantable one or more cells and/or tissues; and (c) a first tubing for conducting a gas generated by the electrolytic gas generator to the container.

According to another aspect of the invention, there is provided an implant system, the implant system comprising (a) at least one of the types of electrolytic gas generators described above; (b) a container for holding implantable one or more cells and/or tissues; (c) a first tubing for conducting hydrogen generated by the electrolytic gas generator to the container; and (d) a second tubing for conducting oxygen generated by the electrolytic gas generator to the container.

For purposes of the present specification and claims, various relational terms like "top," "bottom," "proximal," "distal," "upper," "lower," "front," and "rear" may be used to describe the present invention when said invention is positioned in or viewed from a given orientation. It is to be understood that, by altering the orientation of the invention, certain relational terms may need to be adjusted accordingly.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numeral represent like parts:

FIG. 5 is a schematic section view of an alternate anode current collector constructed according to the present invention, the alternate anode current collector being suitable for use in either the electrolytic gas generator of FIG. 1 or the electrolytic gas generator of FIG. 3, the alternate current collector being shown with its electrically-conductive diaphragm in a flattened state as would be the case when the electrolytic gas generator is in an operating (or "on") state;

FIG. 6 is a schematic section view of the alternate anode current collector of FIG. 5, with its electrically-conductive diaphragm being shown in a distended state as would be the case when the electrolytic gas generator is in a non-operating (or "off") state;

DETAILED DESCRIPTION OF THE INVENTION

Figure 1:
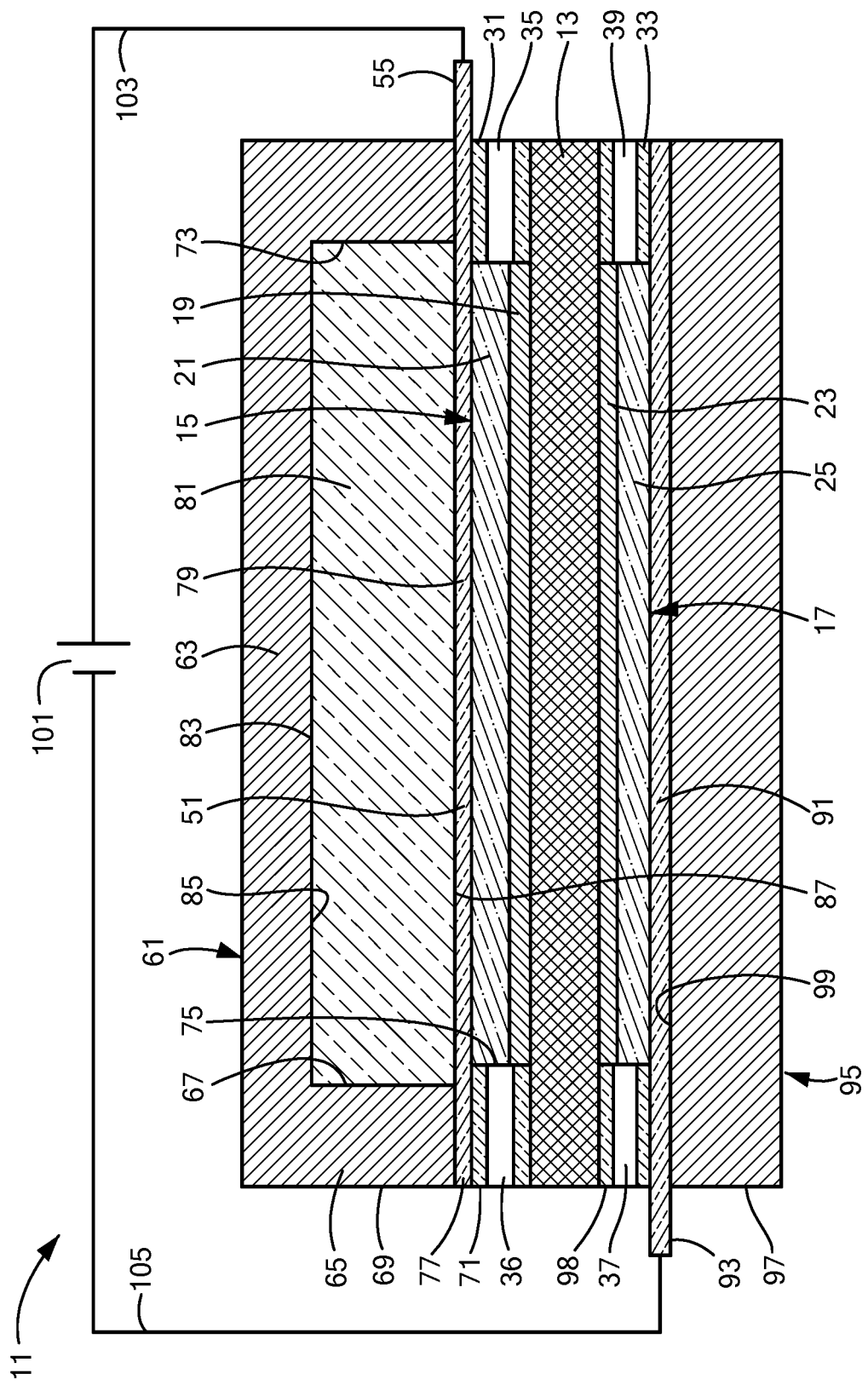
FIG. 1 is a schematic section view of a first embodiment of an electrolytic gas generator constructed according to the present invention, the electrolytic gas generator being shown in an operating (or "on") state.

The present invention is directed, in part, at a novel electrolytic gas generator and is also directed, in part, at an implant system comprising said novel electrolytic gas generator.

Without reducing the present invention to a singular principle, an important concept of the present invention is the design of an electrolytic gas generator that automatically undergoes one or more mechanical changes, such as a physical deformation of one or more components, during the course of electrolysis. More specifically, as current passes through the electrolytic gas generator of the present invention, products are generated at the anode and/or at the cathode, and electrolyte may also be transferred from one electrode to the other via electro-osmosis. In the case of water electrolysis, one or both of the gaseous products of hydrogen and oxygen that are generated by electrolysis may accumulate within the electrolytic gas generator if they do not exit the generator as quickly as they are generated. The accumulation of such gases within the electrolytic gas generator may result in an increased pressure in one or both electrode compartments, and this increase in pressure may, in turn, cause a mechanical change in certain components within the electrolytic gas generator. This electrolysis-induced mechanical change may then be taken advantage of to limit the extent of further electrolysis, as the mechanical change may be engineered to cause two electrically-conductive elements in the electrolytic gas generator that were in physical contact with one another to become partially or completely disconnected from one another. This disconnection may reduce or stop current flow, at which point the generated gas or gases may remain in their respective cell compartments until either they exit the electrolytic gas generator through their respective outlet ports and/or they diffuse through one or more permeable layers in the electrolytic gas generator to the surrounding environment. Thereafter, when the gas pressure in the affected cell compartment decreases, the mechanical change may automatically reverse, and the electrically-conductive elements that had become disconnected may become electrically reconnected, whereby further electrolysis may ensue. In such a way, the electrolytic gas generator of the present invention may be capable of maintaining a constant gas activity in its vicinity so as to maintain cytoprotective, respiratory, and/or metabolic function of vicinal tissue or another implant and may do so with only a connection to an electrical source, such as a source of constant DC current. The constant DC current source, such as a battery, may be co-implanted with the electrolytic gas generator or may be maintained outside the body and wired to the electrolytic gas generator percutaneously. Such a system could optionally be fitted with a secondary control system which, upon detection that the electrolytic gas generator has been de-actuated (i.e., by use of a current sensor), either slows the re-actuation process or prevents it entirely (i.e., latches the circuit open) to satisfy performance or safety criteria.

The electrolytic gas generator of the present invention is particularly amenable to a fully implanted medical device where oxygen is delivered by diffusion (i.e., via gas-permeable membranes) to cells or tissue in one or more implanted, immunoisolated capsules at rates governed by the metabolic consumption rate of said cells or tissue. In these scenarios, it is important to control oxygen pressure to accurately control dose, to mitigate the possible effects of hypoxia and hyperoxia, and to minimize power consumption and system complexity of a fully implanted system. It shall be readily appreciated that the principles taught in the present application are equally applicable to an electrolytic gas generator wherein the gas generated under intrinsic pressure control is hydrogen at the cathode, or moreover, any anodically or cathodically produced electrolytic product gas.

The intrinsic pressure management capability of the present invention is preferred or complementary in critical applications, such as implanted medical devices, to other pressure control methods, including but not limited to closed-loop process controller (pressure sensor plus current controller), external pressure switch, or pressure relief valve, due to the ability to control gas generation at its source (thereby precluding the risk of gas pressure buildup in the electrolytic gas generator in the case of a gas blockage in tubing intervening between said generator and these example extrinsic pressure management solutions). It will be readily appreciated that elimination of a pressure sensor and process controller, or any additional electronic component, comprises a simplification of an overall system which may result in smaller size, lower cost, and higher reliability. It will also be readily appreciated that the use of pressure relief valves is generally precluded in implanted (or otherwise partially enclosed) applications, as there is not a readily convenient or safe location to shunt excess gas generated during valve actuation. It will additionally be appreciated that the present invention affords an additional advantage over other methods of gas generation in implanted or otherwise partially contained applications, in that it may safely account for variations in ambient (i.e., barometric) pressure that would otherwise potentially put implant, subject, or host device at risk due to excessive pressure differential. To these ends, the present invention is an improvement for implanted medical and many other applications, as it enables these simplifications without unduly compromising safety, reliability, size, cost or effectiveness.

Beyond the aforementioned implantable device use, any application requiring in situ pressure-controlled generation of gas reagents in a small, intrinsically-safe, and/or reliable device may benefit from the teachings of this invention. Such alternative applications may include, for instance, corrosion inhibition or acceleration, odor control, cleansing and/or sanitization of surfaces or enclosed spaces, life support of immobilized or enclosed organisms, and reagent production for miniature sensors.

Figure 2:
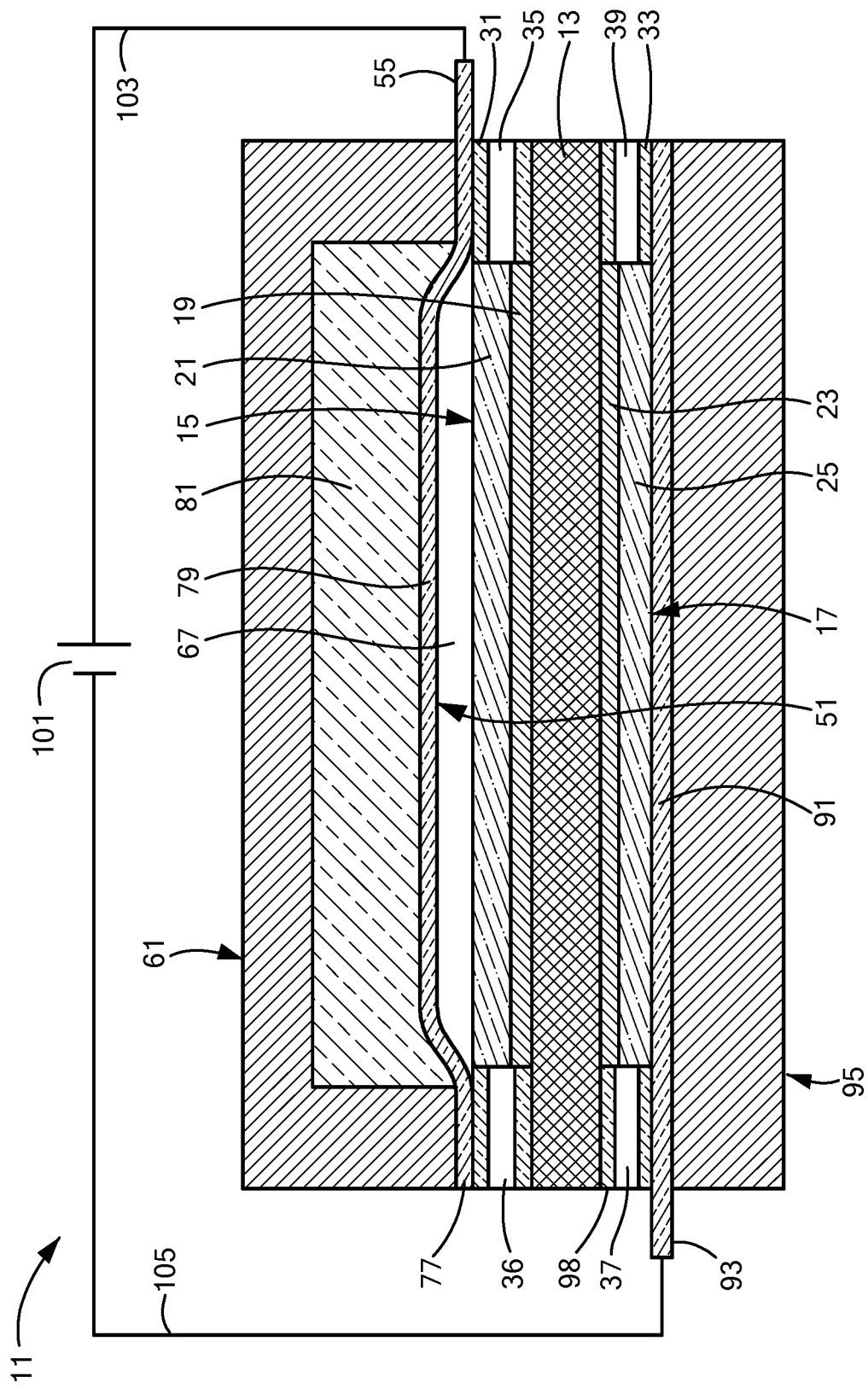
FIG. 2 is a schematic section view of the electrolytic gas generator of FIG. 1, the electrolytic gas generator being shown in a non-operating (or "off") state.

Referring now to FIGS. 1 and 2, there are shown schematic section views of a first embodiment of an electrolytic gas generator constructed according to the present invention, the electrolytic gas generator being represented generally by reference numeral 11. (For simplicity and clarity, certain components of electrolytic gas generator 11 that are not critical to an understanding of the present invention are either not shown or described herein or are shown and/or described herein in a simplified manner.)

Electrolytic gas generator 11, which may be in the form of a water electrolyzer, may comprise a solid polymer electrolyte membrane (PEM) 13 (also known in the art as a proton exchange membrane). Polymer electrolyte membrane 13 is preferably a non-porous, ionically-conductive, electrically-non-conductive, liquid-permeable and substantially gas-impermeable membrane. Polymer electrolyte membrane 13 may consist of or comprise a homogeneous perfluorosulfonic acid (PFSA) polymer. Said PFSA polymer may be formed by the copolymerization of tetrafluoroethylene and perfluorovinylether sulfonic acid. See e.g., U.S. Pat. No. 3,282,875, inventors Connolly et al., issued Nov. 1, 1966; U.S. Pat. No. 4,470,889, inventors Ezzell et al., issued Sep. 11, 1984; U.S. Pat. No. 4,478,695, inventors Ezzell et al., issued Oct. 23, 1984; and U.S. Pat. No. 6,492,431, inventor Cisar, issued Dec. 10, 2002, all of which are incorporated herein by reference in their entireties. A commercial embodiment of a PFSA polymer electrolyte membrane is manufactured by The Chemours Company FC, LLC (Fayetteville, N.C.) as NAFION™ extrusion cast PFSA polymer membrane.

Polymer electrolyte membrane 13 may be a generally planar unitary structure in the form of a continuous film or sheet. In the present embodiment, when viewed from above or below, polymer electrolyte membrane 13 may have a generally circular shape. Moreover, the overall shape of electrolytic gas generator 11, when viewed from above or below, may correspond generally to the shape of polymer electrolyte membrane 13. However, it is to be understood that polymer electrolyte membrane 13, as well as electrolytic gas generator 11 as a whole, is not limited to a generally circular shape and may have a generally rectangular shape or other suitable shape.

Electrolytic gas generator 11 may further comprise an anode 15 and a cathode 17. Anode 15 and cathode 17 may be positioned along two opposing major faces of polymer electrolyte membrane 13. In the present embodiment, anode 15 is shown positioned along the top face of polymer electrolyte membrane 13, and cathode 17 is shown positioned along the bottom face of polymer electrolyte membrane 13; however, it is to be understood that the positions of anode 15 and cathode 17 relative to polymer electrolyte membrane 13 could be reversed.

Anode 15 may comprise an anode electrocatalyst layer 19 and an anode support 21. Anode electrocatalyst layer 19 may be positioned in direct contact with polymer electrolyte membrane 13 and, in the present embodiment, is shown as being positioned directly above and in contact with the top of polymer electrolyte membrane 13. Anode electrocatalyst layer 19 defines the electrochemically active area of anode 15 and preferably is sufficiently porous and electrically- and ionically-conductive to sustain a high rate of surface oxidation reaction. Anode electrocatalyst layer 19, which may be an anode electrocatalyst layer of the type conventionally used in a PEM-based water electrolyzer, may comprise electrocatalyst particles in the form of a finely divided electrically-conductive (and, optionally, ionically-conductive) material (e.g., a metal powder) which can sustain a high rate of electrochemical reaction. The electrocatalyst particles are distributed within anode electrocatalyst layer 19 along with a binder, which is preferably ionically-conductive, to provide mechanical fixation.

Anode support 21, which may be an anode support of the type conventionally used in a PEM-based water electrolyzer and may be, for example, a film or sheet of porous titanium, preferably is sufficiently porous to allow fluid (gas and/or liquid) transfer between anode electrocatalyst layer 19 and the anode-side gas port to be discussed below. To this end, anode support 21 may have pore sizes on the order of, for example, approximately 0.001-0.5 mm. Anode support 21 may also contain macroscopic channel features, for example, on the order of 0.2-10 mm to further assist in fluid distribution. In addition, anode support 21 is electrically-conductive to provide electrical connectivity between anode electrocatalyst layer 19 and the anode-side current collector to be discussed below, and anode support 21 is also preferably ionically-non-conductive. Anode support 21 may be positioned in direct contact with anode electrocatalyst layer 19 and, in the present embodiment, is shown as being positioned directly on top of anode electrocatalyst layer 19 such that anode electrocatalyst layer 19 may be sandwiched between and in contact with polymer electrolyte membrane 13 and anode support 21. Anode support 21 may be dimensioned to entirely cover anode electrocatalyst layer 19, and, in fact, anode 15 may be fabricated by depositing anode electrocatalyst layer 19 on anode support 21.

Cathode 17 may comprise a cathode electrocatalyst layer 23 and a cathode support 25. Cathode electrocatalyst layer 23 may be positioned in direct contact with polymer electrolyte membrane 13 and, in the present embodiment, is shown as being positioned directly below and in contact with polymer electrolyte membrane 13. Cathode electrocatalyst layer 23 defines the electrochemically active area of cathode 17 and preferably is sufficiently porous and electrically- and ionically-conductive to sustain a high rate of surface reduction reaction. Cathode electrocatalyst layer 23, which may be a cathode electrocatalyst layer of the type conventionally used in a PEM-based water electrolyzer, may comprise electrocatalyst particles in the form of a finely divided electrically-conductive (and, optionally, ionically-conductive) material (e.g., a metal powder) which can sustain a high rate of electrochemical reaction. The electrocatalyst particles are distributed within cathode electrocatalyst layer 23 along with a binder, which is preferably ionically-conductive, to provide mechanical fixation. The reactants and products involved at anode 15 and cathode 17 implicate ionic species which are mobile throughout the electroactive surface; therefore, an ionically-conductive medium comprising polymer electrolyte membrane 13 and optionally one or more ionically-conductive catalyst binders in electrocatalyst layers 19 and 23 couples the two electrodes and allows ions to flow in support of the overall reaction electrochemistry.

Cathode support 25, which may be a cathode support of the type conventionally used in a PEM-based water electrolyzer and may be, for example, a film or sheet of porous carbon, preferably is sufficiently porous to allow fluid (gas and/or liquid) transfer between cathode electrocatalyst layer 23 and the cathode-side gas port to be discussed below. To this end, cathode support 25 may have pore sizes on the order of, for example, approximately 0.001-0.5 mm. Cathode support 25 may also contain macroscopic channel features, for example, on the order of 0.2-10 mm to further assist in fluid distribution. In addition, cathode support 25 is electrically-conductive to provide electrical connectivity between cathode electrocatalyst layer 23 and the cathode-side current collector to be discussed below, and cathode support 25 is also preferably ionically-non-conductive. Cathode support 25 may be positioned in direct contact with cathode electrocatalyst layer 23 and, in the present embodiment, is shown as being positioned directly below and in contact with cathode electrocatalyst layer 23 such that cathode electrocatalyst layer 23 may be sandwiched between and in contact with polymer electrolyte membrane 13 and cathode support 25. Cathode support 25 may be dimensioned to entirely cover cathode electrocatalyst layer 23, and, in fact, cathode 17 may be fabricated by depositing cathode electrocatalyst layer 23 on cathode support 25.

The combination of polymer electrolyte membrane 13, anode 15, and cathode 17 or the combination of polymer electrolyte membrane 13, anode electrocatalyst layer 19, and cathode electrocatalyst layer 23 may be regarded collectively as a membrane-electrode assembly (MEA).

Electrolytic gas generator 11 may further comprise an anode seal 31 and a cathode seal 33. Anode seal 31, which may be an anode seal of the type conventionally used in a PEM-based water electrolyzer, may be a generally annular or frame-like member mounted around the periphery of anode 15 in a fluid-tight manner. Anode seal 31, which may be made of TEFLON™ polytetrafluoroethylene, ethylene-propylene-diene-monomer (EPDM) rubber, or another similarly suitable material, may be ionically-non-conductive and electrically-non-conductive. Anode seal 31 may also be non-porous and fluid-impermeable, except for a fluid port extending radially outwardly from the inner periphery of anode seal 31 to the outer periphery of anode seal 31. In the present embodiment, the aforementioned fluid port in anode seal 31 may be an oxygen outlet 35. Oxygen outlet 35 may be fluidically connected to a location in need of oxygen via suitable tubing (not shown), which tubing may be equipped with features like sterilization filters and/or check valves to prevent electrolytic gas generator 11 from becoming contaminated by contents of the tubing or from having condensate flow backwards into electrolytic gas generator 11. Where, for example, electrolytic gas generator 11 is implanted in a body, such tubing may be used to fluidically connect oxygen outlet 35 to a container holding implanted cells and/or tissue. Alternatively, such tubing may be eliminated if the container holding implanted cells and/or tissue is permeable to gas and the container is positioned against or sufficiently proximate to oxygen outlet 35.

Anode seal 31 may additionally include a second fluid port extending radially outwardly from the inner periphery of anode seal 31 to the outer periphery of anode seal 31, which second fluid port may be used as a water inlet 36 to supply water to anode 15 from a source external to electrolytic gas generator 11. For example, a water reservoir (not shown), which may be external to electrolytic gas generator 11, may be fluidically connected to water inlet 36 via suitable tubing (not shown) so as to supply water to anode 15. Such tubing may be equipped with features like sterilization filters and/or check valves. Where electrolytic gas generator 11 is implanted in a body, such a water reservoir may also be implanted in the body, or the water reservoir may be positioned external to the body. Alternatively, instead of using a water reservoir, ambient water in the local environment outside of electrolytic gas generator 11 may be supplied to electrolytic gas generator 11 through water inlet 36; however, in this case, it may be desirable to place one or more filters (not shown) over the exterior of water inlet 36 to keep select contaminants in the ambient water from entering water inlet 36 and to prevent anode-generated gas from exiting through water inlet 36.

Cathode seal 33, which may be a cathode seal of the type conventionally used in a PEM-based water electrolyzer, may be a generally annular or frame-like member mounted around the periphery of cathode 17 in a fluid-tight manner. Cathode seal 33, which may be made of TEFLON™ polytetrafluoroethylene, ethylene-propylene-diene-monomer (EPDM) rubber, or another similarly suitable material, may be ionically-non-conductive and electrically-non-conductive. Cathode seal 33 may also be non-porous and fluid-impermeable, except for two fluid ports extending radially outwardly from the inner periphery of cathode seal 33 to the outer periphery of cathode seal 33. In the present embodiment, one of the two fluid ports in cathode seal 33 may be a water inlet 37, which may be used to supply water to cathode 17 from a source external to electrolytic gas generator 11. For example, a water reservoir (not shown), which may be external to electrolytic gas generator 11, may be fluidically connected to water inlet 37 via suitable tubing (not shown) so as to supply water to cathode 17. Such tubing may be equipped with features like sterilization filters and/or check valves. Where electrolytic gas generator 11 is implanted in a body, such a water reservoir may also be implanted in the body, or the water reservoir may be positioned external to the body. Alternatively, instead of using a water reservoir, ambient water in the local environment outside of electrolytic gas generator 11 may be supplied to electrolytic gas generator 11 through water inlet 37; however, in this case, it may be desirable to place one or more filters or flow control valves (not shown) over the exterior of water inlet 37 to keep select contaminants in the ambient water from entering water inlet 37 and to prevent cathode-generated gas from exiting through water inlet 37.

In the present embodiment, the other of the two fluid ports in cathode seal 33 may be a hydrogen outlet 39. Hydrogen outlet 39 may be fluidically connected via suitable tubing (not shown) to a location in need of hydrogen or, if hydrogen is not needed, to a location where hydrogen may be safely expelled. Such tubing may be equipped with features like sterilization filters and/or check valves. Where, for example, electrolytic gas generator 11 is implanted in a body and it is desired to treat implanted or native cells and/or tissue with hydrogen, such tubing coupled to hydrogen outlet 39 may be used to deliver hydrogen to a container holding the implanted cells and/or tissue or may be used to deliver hydrogen to a location proximate to native cells and/or tissue. Where hydrogen treatment is not needed, such tubing can be used to deliver hydrogen to a part of the body where it can be safely expelled; alternatively, if electrolytic gas generator 11 is implanted at a location in a body where hydrogen can safely diffuse from electrolytic gas generator 11 and be expelled from the body without requiring any tubing, such tubing can be omitted.

In the present embodiment, anode 15 and anode seal 31 may be dimensioned to jointly match the footprint of the top surface of polymer electrolyte membrane 13, and cathode 17 and cathode seal 33 may be dimensioned to jointly match the footprint of the bottom surface of polymer electrolyte membrane 13. Notwithstanding the above, it is to be understood that the footprints of the foregoing components may be varied from what is described above.

Electrolytic gas generator 11 may further comprise an anode current collector 51. Anode current collector 51, which may be a unitary structure in the form of a continuous film or sheet, may be a non-porous, electrically-conductive, flexible, diaphragm-like member capable of being reversibly deformed (for example, when subjected to gas pressure) from a generally planar state to a bulging or distended state. When viewed from above, anode current collector 51 may have a footprint that substantially matches the collective footprints of anode 15 and anode seal 31, except that anode current collector 51 may additionally comprise a tab 55 that may extend radially outwardly a short distance beyond the footprint of anode seal 31 and that may be used as a terminal. In the present embodiment, anode current collector 51 is preferably substantially gas-impermeable. In addition, in the present embodiment, anode current collector 51 is preferably elastic but need not be. Examples of materials that may be suitable for use as anode current collector 51 include, but are not limited to, silicones films or sheets with metallic (e.g., silver) or other electrically-conductive particles dispersed therein and non-porous, electrically-conductive, liquid-permeable, substantially gas-impermeable membranes of the type disclosed in U.S. Pat. No. 9,595,727 B2, inventors Mittelsteadt et al., which issued Mar. 14, 2017, and which is incorporated herein by reference in its entirety.

More specifically, according to the aforementioned patent (hereinafter "the '727 patent"), such a non-porous, electrically-conductive, liquid-permeable, substantially gas-impermeable membrane may comprise, for example, a solid polymer electrolyte into which electrically-conductive materials are dispersed. Examples of materials suitable for use as the solid polymer electrolyte may include (i) polymer compositions that contain metal salts; (ii) polymeric gels that contain electrolytes; and (iii) ion exchange resins. More specifically, the solid polymer electrolyte may be, for example, a cation exchange ionomer membrane where the cation exchange group may be, but is not limited to, $-SO_3^-$, $-SO_2NH^+$, $-PO_3^{2-}$, or $-CO_2^-$ or may be, for example, an anion exchange ionomer membrane where the anion exchange group may be, but is not limited to, $-NH_2^+$. A preferred material for use as the solid polymer electrolyte may be a perfluorosulfonic acid (PFSA) membrane, such as is manufactured by The Chemours Company FC, LLC (Fayetteville, N.C.) as NAFION™ extrusion cast PFSA polymer membrane. Examples of other materials that may be used in place of NAFION™ PFSA are disclosed in U.S. Pat. No. 7,947,405 B2, inventors Mittelsteadt et al., which issued May 24, 2011, and which is incorporated herein by reference in its entirety.

Examples of materials that may be suitable for use as the dispersed, electrically-conductive materials of the above-described membrane may include high-aspect-ratio, electrically-conductive, non-particulate materials, such as carbon nanotubes, carbon nanofibers, metal nanowires, or combinations thereof. Carbon nanotubes that may be suitable for use in the membrane may have a diameter of about 0.20 nm to about 100 nm, may have a length of about 0.50 μm to about 200 μm, and may have an aspect ratio (i.e., length/diameter) in the range of about 5 to about 1,000,000. Additionally, carbon nanotubes that may be suitable for use in the membrane may be non-functionalized or may include one or more functional groups, such as, but not limited to, $-COOH$, $-PO_4^-$, $-SO_3H$, $-SH$, $-NH_2$, tertiary amines, quaternary amines, $-CHO$, $-OH$, $-NO_2$, and $-PO_3^{2-}$. Moreover, carbon nanotubes that may be suitable for use in the membrane may include single-walled carbon nanotubes, double-walled carbon nanotubes, multi-walled carbon nanotubes, or combinations thereof.

Carbon nanofibers that may be suitable for use in the membrane may be non-functionalized or may include one or more functional groups, such as, but not limited to, $-COOH$, $-PO_4^-$, $-SO_3H$, $-SH$, $-NH_2$, tertiary amines, quaternary amines, $-CHO$, $-OH$, $-NO_2$, and $-PO_3^{2-}$. In addition to including dispersed, non-particulate, electrically-conductive materials or instead of such materials, the membrane may comprise dispersed, electrically-conductive particles, such as, but not limited to, carbon black, metal particles (e.g., niobium particles, platinum particles, titanium particles, or combinations thereof), supported metal particles, or combinations thereof.

The above-described membrane may be prepared by adding the electrically-conductive materials to the ionomer while the ionomer is in suspension form and then drying the suspension.

Electrolytic gas generator 11 may further comprise an anode endplate 61. Anode endplate 61, which may be a unitary structure made of a rigid material of the type conventionally used in PEM-based water electrolyzers, such as a suitably strong metal or polymer, may have the shape of an inverted canister and may comprise a top wall 63 and a side wall 65 jointly defining an interior chamber 67 with an open bottom. Anode endplate 61 may be appropriately dimensioned so that an outer surface 69 of side wall 65 may be substantially aligned with an outer surface 71 of anode seal 31. In addition, anode endplate 61 may be further dimensioned so that an inner surface 73 of side wall 65 may be spaced radially outwardly relative to an inner surface 75 of anode seal 31. A vascularizing membrane (not shown), such as disclosed in U.S. Patent Application Publication No. US 2015/0112247 A1, may be applied to one or more exposed surfaces of anode endplate 61.

The bottom of side wall 65 of anode endplate 61 may be positioned directly on top of anode current collector 51 and may be used to secure a peripheral portion 77 of anode current collector 51 between anode endplate 61 and anode seal 31 (peripheral portion 77 of anode current collector 51 being positioned directly on top of anode seal 31). In this manner, peripheral portion 77 of anode current collector 51 may be kept immobile between anode endplate 61 and anode seal 31 whereas a central portion 79 of anode current collector 51 may be free to flex upwardly away from anode 15 when a particular anodic gas pressure is reached between anode current collector 51 and anode 15, as will be discussed further below. As can readily be appreciated, when central portion 79 of anode current collector 51 flexes upwardly away from anode 15 sufficiently that anode current collector 51 and anode 15 are no longer in electrical contact with one another, electrolytic gas generator 11 stops electrolyzing.

Electrolytic gas generator 11 may further comprise a resiliently-compressible member 81. Resiliently-compressible member 81 may be a structure designed to permit central portion 79 of anode current collector 51 to deform or to distend upwardly away from and out of contact with anode 15 when the gas pressure between anode current collector 51 and anode 15 exceeds a certain threshold gas pressure and to cause or to bias central portion 79 of anode current collector 51 to flatten or to deflate downwardly back into contact with anode 15 when the gas pressure between anode current collector 51 and anode 15 falls below a certain threshold gas pressure. The threshold gas pressure at which resiliently-compressible member 81 may permit central portion 79 to flex away from anode 15 and the threshold gas pressure at which resiliently-compressible member 81 may cause central portion 79 to flex back into contact with anode 15 may be the same or may be different. In some cases, it may be advantageous for the threshold gas pressure at which resiliently-compressible member 81 allows central portion 79 to flex away from anode 15 to be significantly greater than the threshold gas pressure at which resiliently-compressible member 81 forces central portion 79 to flex back into contact with anode 15. Consequently, in such a case, once the operation of electrolytic gas generator 11 has stopped, it will not resume until the gas pressure between central portion 79 and anode 15 has dropped significantly. In this manner, electrolytic gas generator 11 may be prevented from undesirably stuttering back and forth between its operating and off states.

In the present embodiment, resiliently-compressible member 81 may comprise a block or disc of foam that may be disposed within interior chamber 67 of anode endplate 61. Such a foam may be a closed-cell foam or an open-cell foam. Examples of suitable foams may include, but are not limited to, polyurethane foams and silicone rubber foams, such as an open-cell silicone rubber foam. Resiliently-compressible member 81 may be appropriately dimensioned to have a first surface 83 engaged with an inner surface 85 of top wall 63 of anode endplate 61 and a second surface 87 engaged with anode current collector 51. In the present embodiment, resiliently-compressible member 81 may be dimensioned so that, when in its uncompressed state, it substantially fills the entire volume of interior chamber 67 of anode endplate 61; however, it is to be understood that resiliently-compressible member 81 need not be so dimensioned.

Although, in the present embodiment, resiliently-compressible member 81 may be a block of foam, resiliently-compressible member 81 is not limited thereto and may be any type of resiliently-compressible structure, such as, but not limited to, a coil spring, a Belleville spring, an enclosed gas pocket, a gas pocket with an externally referenceable gas filling port, or combinations thereof.

Also, it is to be understood that, if anode current collector 51 is sufficiently inherently resilient, it may be possible to omit resiliently-compressible member 81.

Electrolytic gas generator 11 may further comprise a cathode current collector 91, which may be a cathode current collector of the type conventionally used in a PEM-based water electrolyzer and may be, for example, a platinum-coated titanium sheet. When viewed from below, cathode current collector 91 may have a footprint that substantially matches the collective footprints of cathode 17 and cathode seal 33, except that cathode current collector 91 may additionally comprise a tab 93 that may extend radially outwardly a short distance beyond the footprint of cathode seal 33 and that may be used as a terminal.

Electrolytic gas generator 11 may further comprise a cathode endplate 95, which may be a cathode endplate of the type conventionally used in a PEM-based water electrolyzer. Cathode endplate 95 may be appropriately dimensioned so that a side wall 97 thereof may be substantially aligned with an outer surface 98 of cathode seal 33. A top wall 99 of cathode endplate 95 may be positioned directly below cathode current collector 91 and may be used to keep cathode current collector 91 in direct contact with cathode 17 and with cathode seal 33. A vascularizing membrane (not shown), such as disclosed in U.S. Patent Application Publication No. US 2015/0112247 A1, may be applied to one or more exposed surfaces of cathode endplate 95.

Electrolytic gas generator 11 may further comprise a power source 101. Power source 101, which may be, for example, a DC battery (which may be rechargeable), may be electrically connected by a wire 103 to tab 55 of anode current collector 51 and by a wire 105 to tab 93 of cathode current collector 91. Where, for example, electrolytic gas generator 11 is implanted in a patient, power source 101 may also be implanted in the patient; alternatively, power source 101 may be positioned external to the patient.

Electrolytic gas generator 11 may further comprise other components commonly found in conventional PEM-based water electrolyzers. For example, the static forces upon electrolytic gas generator 11 that may be required to compress resiliently-compressible member 81, to sustain good electrical contact of the serial components of electrolytic gas generator 11, and to achieve good sealing of the cell perimeter may be established and maintained using a variety of conventional fixturing or joining implements and techniques about the internal or external periphery of the assembly. Such implements may include, for instance, fasteners (e.g., screws, rivets, etc.) which may clamp the endplates 61 and 95 together, or adhesives, cements or welds which cohere the elements together in the seal region. Such implements and techniques are considered to be known to those of ordinary skill in the art.

Referring now specifically to FIG. 1, it can be seen that electrical contact is established across the combination of anode current collector 51, anode 15, polymer electrolyte membrane 13, cathode 17, and cathode current collector 91. As a result, electrolytic gas generator 11 forms a closed electrical circuit, and electrolytic gas generator 11 is in an operating (or "on") state for the electrolysis of water. Water may be introduced into electrolytic gas generator 11 through water inlet 36 of anode seal 31 and/or water inlet 37 of cathode seal 33, and such water may be electrolyzed in the conventional manner at the electroactive interfaces of electrolytic gas generator 11, with oxygen gas being generated at the interface of polymer electrolyte membrane 13 and anode electrocatalyst layer 19 and with hydrogen gas being generated at the interface of polymer electrolyte membrane 13 and cathode electrocatalyst layer 23. The thus-generated oxygen gas may then exit electrolytic gas generator 11 through oxygen outlet 35, and the thus-generated hydrogen gas may then exit electrolytic gas generator 11 through hydrogen outlet 39. If the rate at which oxygen gas may exit electrolytic gas generator 11 is greater than or approximately equal to the rate at which oxygen gas is generated by electrolytic gas generator 11, very little, if any, oxygen gas may build up between anode support 21 and anode current collector 51, and the upwardly-directed gas pressure exerted on anode current collector 51 may be less than the downwardly-directed mechanical pressure exerted on anode current collector 51 by resiliently-compressible member 81. As a result, electrical contact may be maintained between anode current collector 51 and anode support 21, and gas generation may continue.

On the other hand, if the rate at which oxygen gas may exit electrolytic gas generator 11 is less than the rate at which oxygen gas is generated by electrolytic gas generator 11, oxygen gas may build up between anode support 21 and anode current collector 51, and, eventually, the upwardly-directed gas pressure exerted on anode current collector 51 may be greater than the downwardly-directed mechanical pressure exerted on anode current collector 51 by resiliently-compressible member 81. As a result, as seen in FIG. 2, anode current collector 51 may flex or distend away from anode support 21, thereby breaking any electrical contact between anode current collector 51 and anode support 21. As a result, electrolytic gas generator 11 may stop electrolyzing water. Thereafter, at least some of the oxygen gas that has accumulated between anode support 21 and anode current collector 51 may exit electrolytic gas generator 11 through oxygen outlet 35 until the gas pressure between anode support 21 and anode current collector 51 decreases sufficiently for anode current collector 51 to be brought back into contact with anode support 21, thereby permitting electrolysis to resume.

As can be appreciated, the foregoing scenario may take place in the context of a cell implant system in which the oxygen produced by electrolytic gas generator 11 is conducted by tubing to a closed container holding implanted cells and/or tissue. If the implanted cells and/or tissue cannot consume the oxygen that is delivered thereto at a rate that exceeds or is substantially equal to the rate at which the generated oxygen is delivered or if there is some restriction to flow downstream of oxygen outlet 35, oxygen may accumulate in the electrolytic gas generator 11 as described above. If the amount of oxygen that accumulates within electrolytic gas generator 11 is sufficient to create a pressure that exceeds a predetermined threshold, electrolytic gas generator 11 stops generating oxygen. In this manner, electrolytic gas generator 11 may be regarded as being self-regulating. As can be appreciated, such a self-regulating electrolytic gas generator is advantageous for at least the reason that it does not require external sensors or feedback mechanisms.

Figure 3:
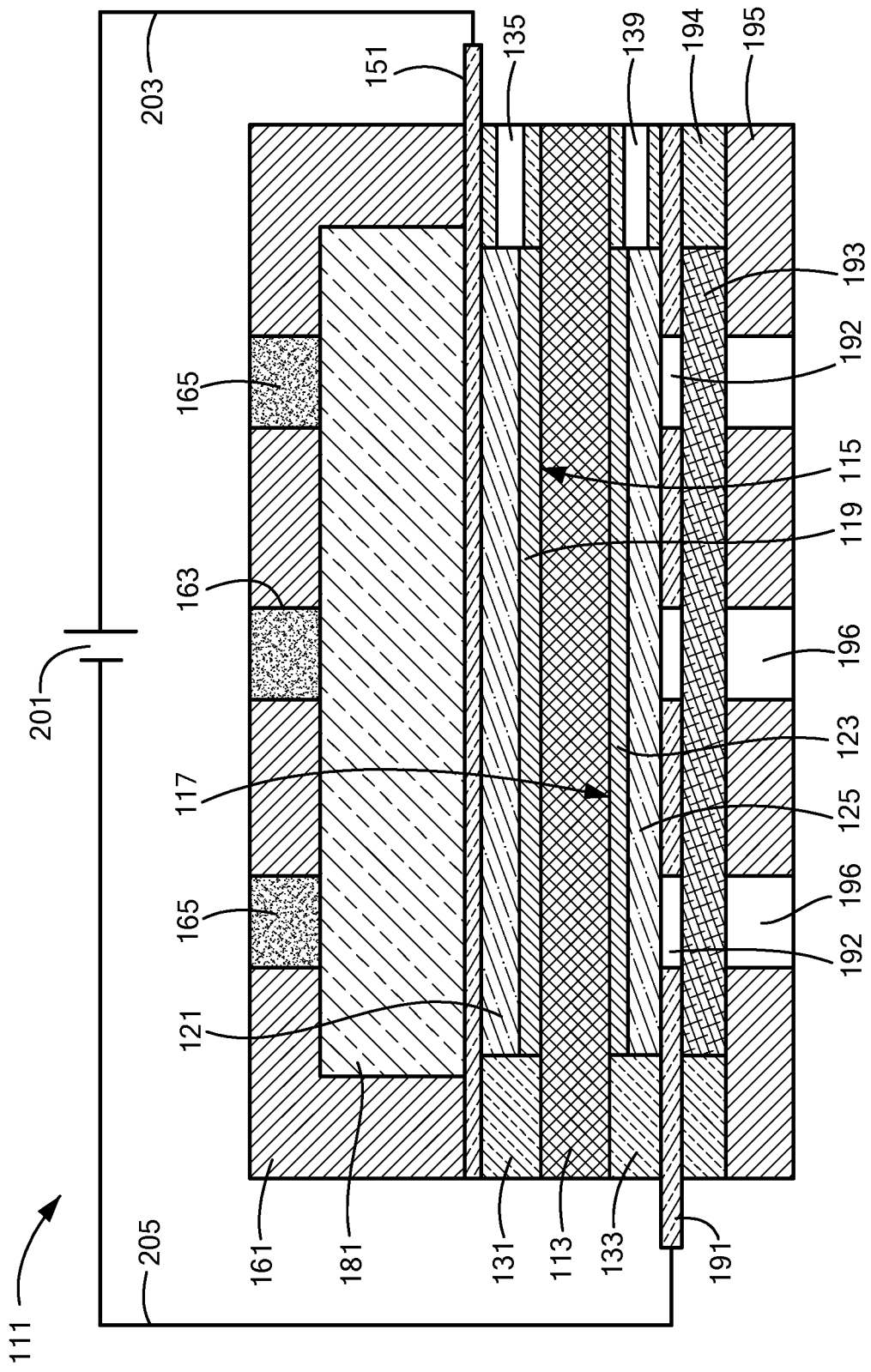
FIG. 3 is a schematic section view of a second embodiment of an electrolytic gas generator constructed according to the present invention, the electrolytic gas generator being shown in an operating (or "on") state.
Figure 4:
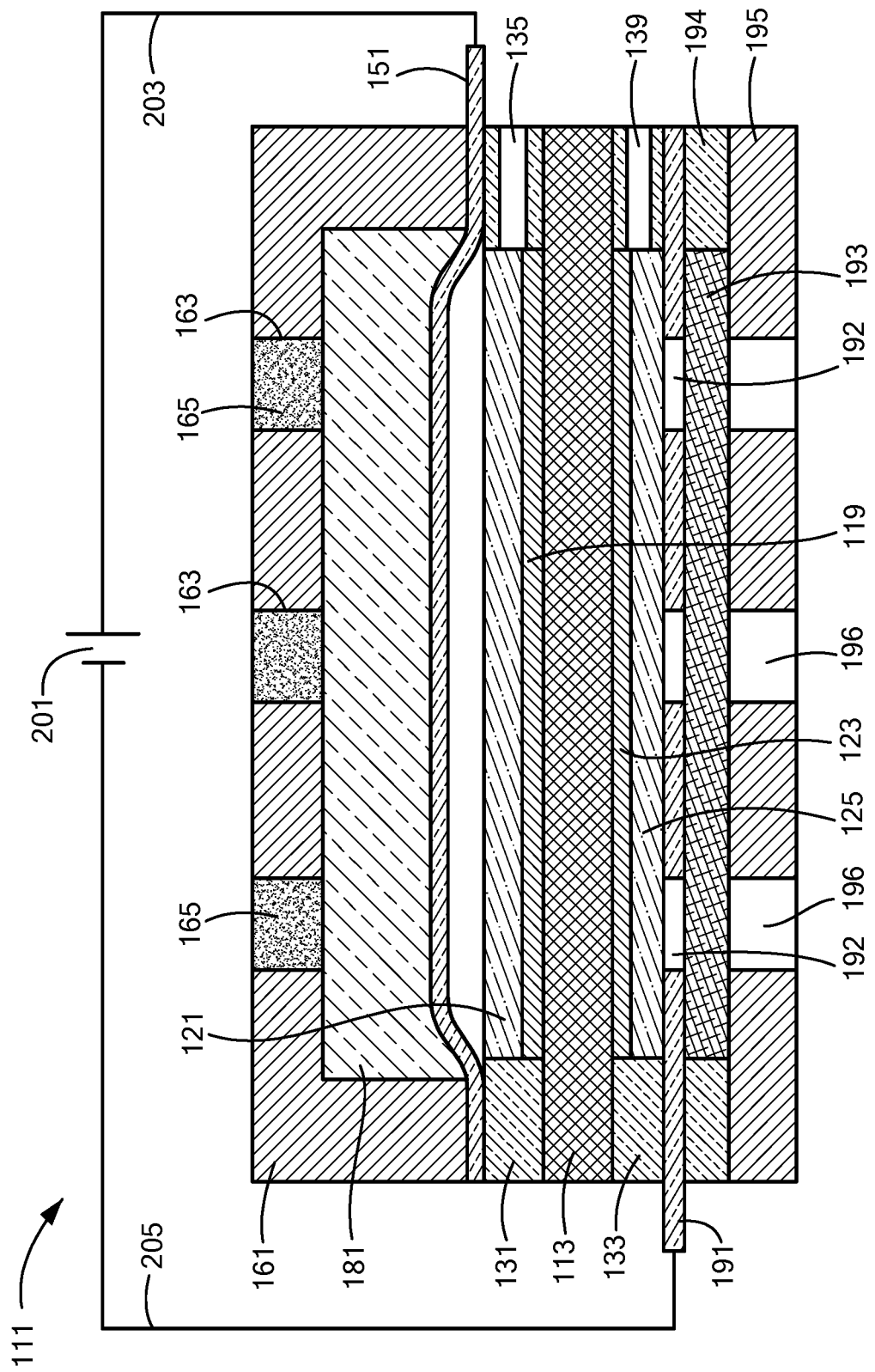
FIG. 4 is a schematic section view of the electrolytic gas generator of FIG. 3, the electrolytic gas generator being shown in a non-operating (or "off") state.

Referring now to FIGS. 3 and 4, there are shown schematic section views of a second embodiment of an electrolytic gas generator constructed according to the present invention, the electrolytic gas generator being represented generally by reference numeral 111. (For simplicity and clarity, certain components of electrolytic gas generator 111 that are not critical to an understanding of the present invention are either not shown or described herein or are shown and/or described herein in a simplified manner.)

Electrolytic gas generator 111, which may be in the form of a water electrolyzer, may be similar in many respects to electrolytic gas generator 11. Accordingly, electrolytic gas generator 111 may comprise a polymer electrolyte membrane 113, which may be identical to polymer electrolyte membrane 13. In addition, electrolytic gas generator 111 may also comprise an anode 115 comprising an anode electrocatalyst layer 119 and an anode support 121, wherein anode 115, anode electrocatalyst layer 119, and anode support 121 may be identical to anode 15, anode electrocatalyst layer 19, and anode support 21, respectively, of electrolytic gas generator 11. Moreover, electrolytic gas generator 111 may further comprise a cathode 117 comprising a cathode electrocatalyst layer 123 and a cathode support 125, wherein cathode 117, cathode electrocatalyst layer 123 and cathode support 125 may be identical to cathode 17, cathode electrocatalyst layer 23, and cathode support 25, respectively, of electrolytic gas generator 11.

Electrolytic gas generator 111 may further comprise an anode seal 131 and a cathode seal 133. Anode seal 131 may be similar in most respects to anode seal 31, with a principal difference between the two anode seals being that, whereas anode seal 31 may comprise oxygen outlet 35 and water inlet 36, anode seal 131 may comprise an oxygen outlet 135 but need not include a water inlet. In fact, it may even be possible, in certain cases, for anode seal 131 not to include oxygen outlet 135. Cathode seal 133 may be similar in most respects to cathode seal 33, with a principal difference between the two cathode seals being that, whereas cathode seal 33 may comprise water inlet 37 and hydrogen outlet 39, cathode seal 133 may comprise a hydrogen outlet 139 but need not include a water inlet.

Electrolytic gas generator 111 may further comprise an anode current collector 151. Anode current collector 151 may be similar in most respects to anode current collector 51, with a principal difference between the two anode current collectors being that, whereas anode current collector 51 may be substantially gas-impermeable, anode current collector 151 is gas-permeable. Anode current collector 151 is also preferably liquid-permeable.

Electrolytic gas generator 111 may further comprise an anode endplate 161. Anode endplate 161 may be similar in most respects to anode endplate 61, with a principal difference between the two endplates being that, whereas anode endplate 61 may be made of a non-porous, fluid-impermeable material, anode endplate 161 may comprise a porous or fluid-permeable material. For example, in the present embodiment, anode endplate 161 may comprise one or more pores 163. Pores 163 may permit the passage of gas or liquid from the external environment of anode endplate 161 to the internal chamber of anode endplate 161 or vice versa. (In addition, pores 163 may allow pressure equalization with the local external pressure.) For example, outside water may be introduced into the anode side of electrolytic gas generator 111 through pores 163, and oxygen gas generated at anode 115 may be expelled from electrolytic gas generator 111 through pores 163. An ultrafiltration membrane 165 or other suitable membrane or filter may be positioned within pores 163 to keep select contaminants from passing from the exterior of electrolytic gas generator 111 through pores 163 into the interior chamber of anode endplate 161. (It is to be understood that, instead of or in addition to having ultrafiltration membrane 165 positioned within pores 163, ultrafiltration membrane 165 may be positioned across pores 163 along the exterior or interior surface of anode endplate 161.) A vascularizing membrane (not shown), such as disclosed in U.S. Patent Application Publication No. US 2015/0112247 A1, may be applied to one or more exposed surfaces of anode endplate 161.

Where, for example, electrolytic gas generator 111 is implanted in a patient, oxygen gas expelled through pores 163 may be delivered to a desired destination via one or more tubes coupled to pores 163. Alternatively, electrolytic gas generator 111 may be positioned near or at a desired destination, and expelled gas may simply diffuse to the desired destination without the use of tubing. In fact, according to one embodiment, a gas-permeable wall of a container holding implanted cells and/or tissue may be directly contacted with the exterior of anode endplate 161 so that oxygen expelled from pores 163 may pass directly into the container holding implanted cells and/or tissue.

Electrolytic gas generator 111 may further comprise a resiliently-compressible member 181. Resiliently-compressible member 181 may be similar in most respects to resiliently-compressible member 81, with a principal difference between the two resiliently-compressible members being that, whereas resiliently-compressible member 81 need not be porous or gas-permeable, resiliently-compressible member 181 is preferably porous or gas-permeable to enable oxygen gas generated at anode 115 to pass therethrough. Therefore, for example, resiliently-compressible member 181 may be a suitable open-cell foam.

Electrolytic gas generator 111 may further comprise a cathode current collector 191. Cathode current collector 191 may be similar in most respects to cathode current collector 91, with a principal difference between the two cathode current collectors being that, whereas cathode current collector 91 need not be porous, cathode current collector 191 may comprise one or more pores 192. As will become apparent below, pores 192 may be used to facilitate the passage of outside water to cathode 117.

Electrolytic gas generator 111 may further comprise an interface layer 193. Interface layer 193, which is positioned below and in direct contact with cathode current collector 191, may comprise a liquid-permeable, gas-impermeable material. In this manner, interface layer 193 may facilitate the passage of outside water therethrough to pores 192 of cathode current collector 191 while excluding contaminants (such as biomolecules in said outside water where, for example, electrolytic gas generator 111 is implanted in a patient) and may prevent gas generated at cathode 117 from egressing therethrough. A sealing gasket 194 may be positioned around the periphery of interface layer 193.

Electrolytic gas generator 111 may further comprise a cathode endplate 195. Cathode endplate 195 may be similar in most respects to cathode endplate 95, with a principal difference between the two cathode endplates being that, whereas cathode endplate 95 need not be porous, cathode endplate 195 may comprise one or more pores 196, which may be used to communicate with the local environment and to facilitate the ingress of outside water into electrolytic gas generator 111 for delivery to cathode 117. Where, for example, electrolytic gas generator 111 is implanted in a patient, the outer surfaces of cathode endplate 195 and interface layer 193 may be treated to promote vascular ingrowth and tissue integration. A vascularizing membrane (not shown), such as disclosed in U.S. Patent Application Publication No. US 2015/0112247 A1, may be applied to one or more exposed surfaces of cathode endplate 195.

Electrolytic gas generator 111 may further comprise a power source 201, which may be identical to power source 101. Power source 201 may be electrically connected by a wire 203 to anode current collector 151 and by a wire 205 to cathode current collector 191.

Like electrolytic gas generator 11, electrolytic gas generator 111 may further comprise other components commonly found in conventional PEM-based water electrolyzers.

In use, referring now specifically to FIG. 3, it can be seen that electrical contact is established across the combination of anode current collector 151, anode support 121, anode electrocatalyst layer 119, polymer electrolyte membrane 113, cathode electrocatalyst layer 123, cathode support 125, and cathode current collector 191. As a result, electrolytic gas generator 111 forms a closed electrical circuit, and electrolytic gas generator 111 is in an operating (or "on") state for the electrolysis of water. Water may be introduced into electrolytic gas generator 111 by passing first through pores 163 of anode endplate 161, then through resiliently-compressible member 181, and then through anode current collector 151. In addition, water may also be introduced into electrolytic gas generator 111 by passing through pores 196 of cathode endplate 195, then through interface layer 193, then through pores 192 of cathode current collector 191. Such water may then be electrolyzed in the conventional manner at the electroactive interfaces of electrolytic gas generator 111, with oxygen gas being generated at the interface of polymer electrolyte membrane 113 and anode electrocatalyst layer 119 and with hydrogen gas being generated at the interface of polymer electrolyte membrane 113 and cathode electrocatalyst layer 123. The thus-generated hydrogen gas may then exit electrolytic gas generator 111 through hydrogen outlet 139.

With respect to thus-generated oxygen gas, a first portion may exit electrolytic gas generator 111 through oxygen outlet 135, a second portion may diffuse through anode current collector 151, then pass through resiliently-compressible material 181, and then pass through pores 163 of anode endplate 161, and a third portion may accumulate between anode current collector 151 and anode support 121. If the gas pressure of the third portion does not exceed the combination of the pressure applied by resiliently-compressive member 181 and the environmental pressure, anode current collector 151 may remain in contact with anode support 121, and electrolysis may continue. On the other hand, if the gas pressure of the third portion exceeds the combination of the pressure applied by resiliently-compressive member 181 and the environmental pressure, anode current collector 151 may be bent out of contact with anode support 121, as seen in FIG. 4, thereby breaking any electrical contact between anode current collector 151 and anode support 121. As a result, electrolytic gas generator 111 may stop electrolyzing water. Thereafter, at least some of the oxygen gas that has accumulated between anode support 121 and anode current collector 151 may dissipate until the gas pressure between anode support 121 and anode current collector 151 decreases sufficiently for anode current collector 151 to be brought back into contact with anode support 121, thereby permitting electrolysis to resume.

Referring now to FIGS. 5 and 6, there are shown schematic section views of an alternate anode current collector constructed according to the present invention, the alternate anode current collector being represented generally by reference numeral 251.

Anode current collector 251, which may be suitable for use in electrolytic gas generator 11, electrolytic gas generator 111, or other electrolytic gas generators operating on similar principles, may be similar in most respects to anode current collector 51 or to anode current collector 151 and may be used similarly to such anode current collectors. A principal difference between anode current collector 251 and anode current collector 51 or anode current collector 151 may be that, whereas anode current collector 51 or 151 may be a one-piece structure, anode current collector 251 may comprise the combination of an electrically-conductive diaphragm 253 and a ring terminal 255. Electrically-conductive diaphragm 253 may be similar in composition to anode current collector 51 or to anode current collector 151. Ring terminal 255, which may be an electrically-conductive member, may be bonded or otherwise fixed to electrically-conductive diaphragm 253. As can be seen in FIG. 5, when in its relaxed state, electrically-conductive diaphragm 253 lies substantially flat. Consequently, with electrically-conductive diaphragm 253 in such a flattened state, anode current collector 251 may be used to maintain an electrolytic gas generator in an operating (or "on" state). By contrast, as can be seen in FIG. 6, electrically-conductive diaphragm 253 may become distended, for example, when subjected to gas pressure and may extend though an opening 257 in ring terminal 255. Consequently, with electrically-conductive diaphragm 253 in such a distended state, anode current collector 251 may move out of electrical contact with its anode, thereby causing the respective electrolytic gas generator to be switched to a non-operating (or "off") state. Thereafter, when electrically-conductive diaphragm 253 is no longer subjected to such gas pressure or when the gas pressure decreases to a certain threshold, electrically-conductive diaphragm 253, due to a biasing force from resiliently-compressible member 81 or 181 and/or due to its own inherent resiliency, may once again assume a flattened state.

Figure 7:
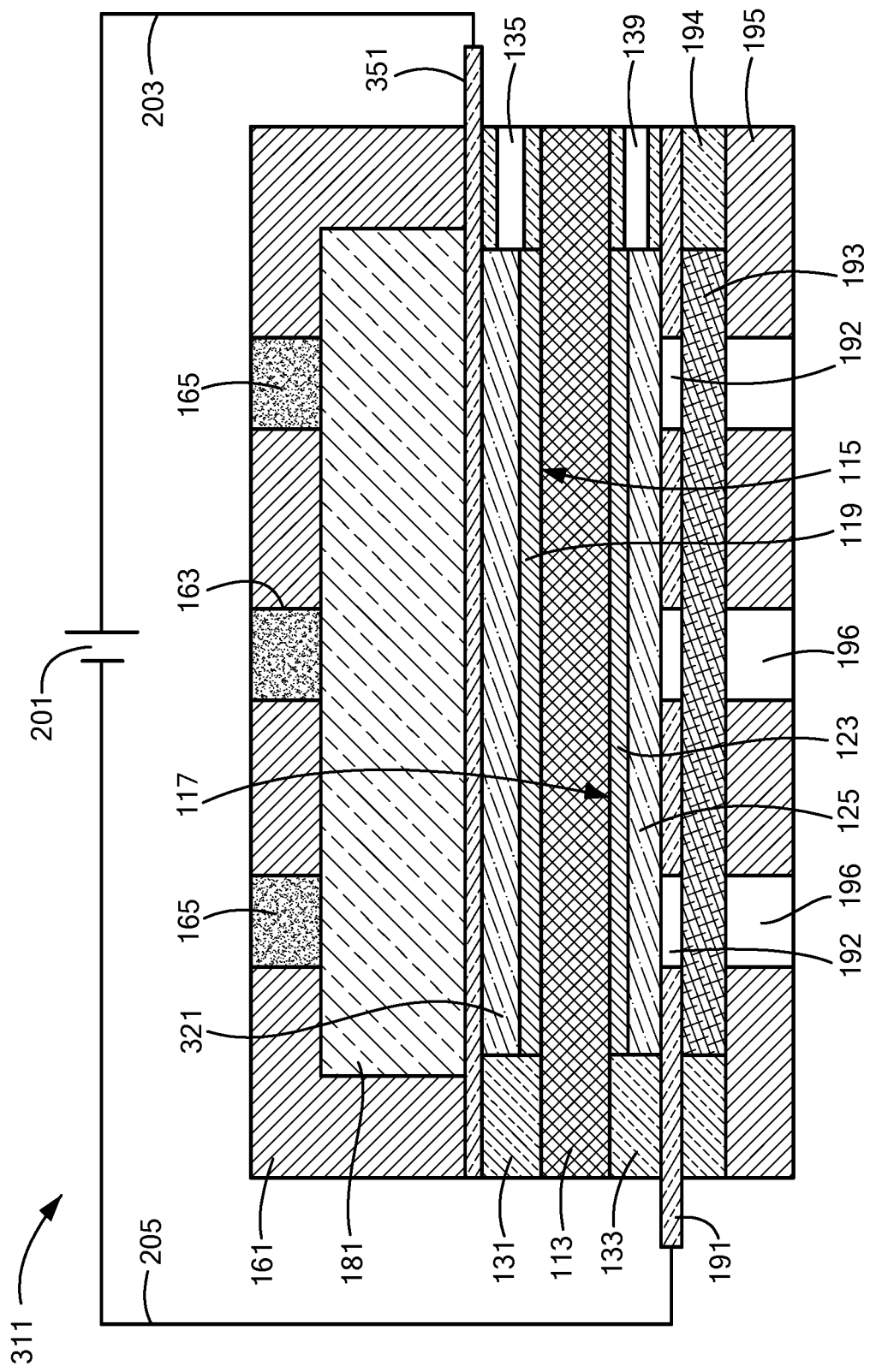
FIG. 7 is a schematic section view of a third embodiment of an electrolytic gas generator constructed according to the present invention, the electrolytic gas generator being shown in a fully-operating state.
Figure 8:
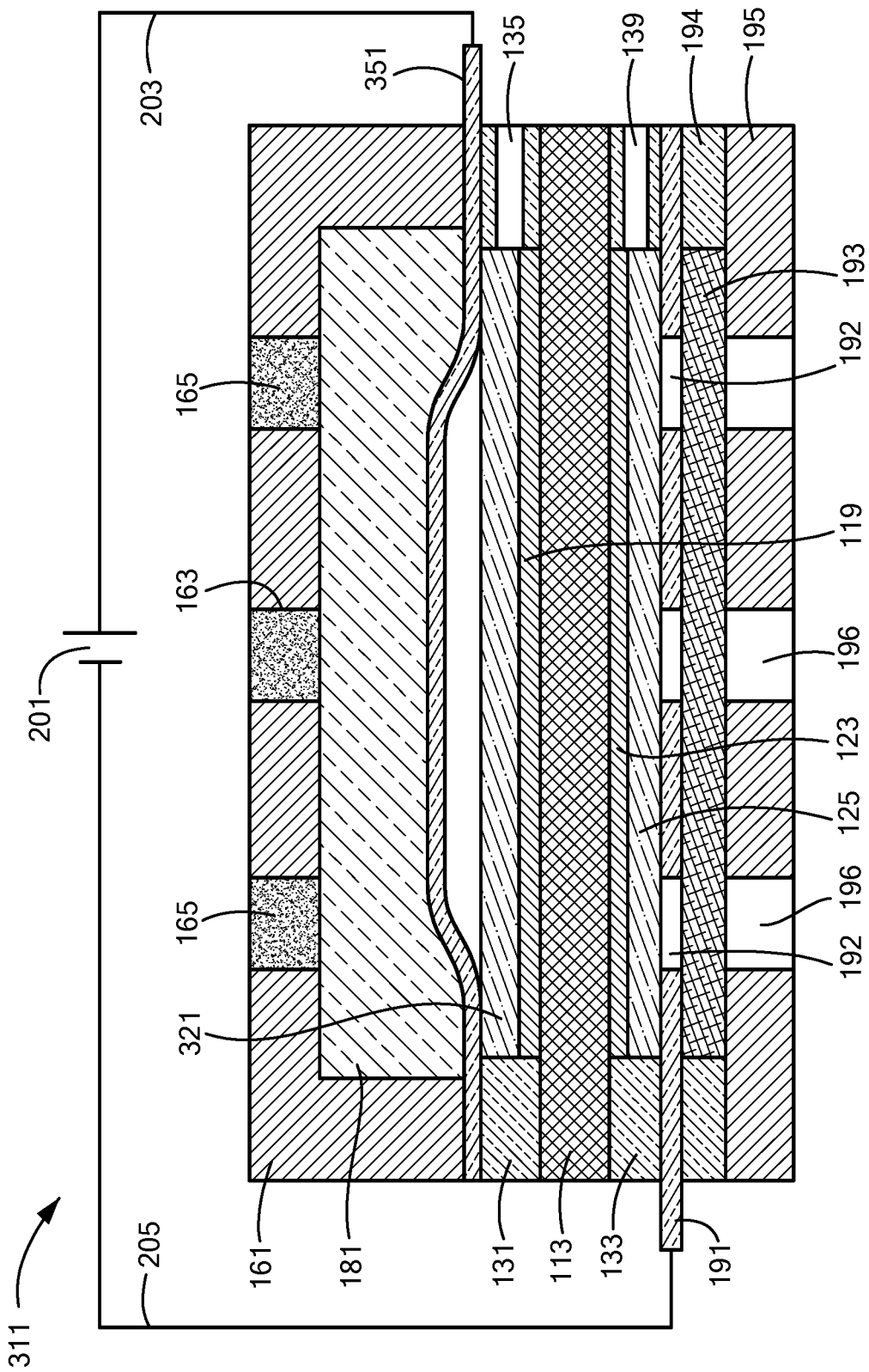
FIG. 8 is a schematic section view of the electrolytic gas generator of FIG. 7, the electrolytic gas generator being shown in a partially-operating state.

Referring now to FIGS. 7 and 8, there are shown schematic section views of a third embodiment of an electrolytic gas generator constructed according to the present invention, the electrolytic gas generator being represented generally by reference numeral 311. (For simplicity and clarity, certain components of electrolytic gas generator 311 that are not critical to an understanding of the present invention are either not shown or described herein or are shown and/or described herein in a simplified manner.)

Electrolytic gas generator 311 may be similar in most respects to electrolytic gas generator 111. A principal difference between the two electrolytic gas generators may be that, whereas electrolytic gas generator 111 may be configured so that anode current collector 151 makes no physical/electrical contact with anode support 121 when the gas pressure between anode current collector 151 and anode support 121 exceeds the combination of the pressure applied by resiliently-compressive member 181 and the environmental pressure, electrolytic gas generator 311 may comprise an anode support 321 and an anode current collector 351 that, under analogous pressure conditions, are configured to maintain some physical/electrical contact with one another, albeit to a diminished extent. Such a state, which may be regarded as a "partially on" condition, results in reduced current through electrolytic gas generator 311, due to the added series resistance imposed by the longer and/or more tortuous conduction path. As a result of such a reduction in current, a reduction in gas production may ensue.

As can be appreciated, an important feature of the present invention is the anode current collector, which sustains variable physical—and, therefore, variable electrical—contact with the anode support in response to differences in pressure on opposing faces of the anode current collector. In opposition to the generated gas pressure, a resiliently-compressible member (e.g., rubber foam) may be implemented on the side of the anode current collector opposite to the side where electrolytic gas generation occurs. The essential components of the electrolytic gas generator may be improved by modification of the current collection scheme to enable a responsiveness to changes in either environmental pressure or the pressure of the generated gas. Physical contact, and, therefore, electrical conductivity, is maintained along the following electrical path: anode current collector to anode support to anode electrocatalyst layer to polymer electrolyte membrane to cathode electrocatalyst layer to cathode support and finally to cathode current collector. This state is considered "on" because the application of electrical power to the two collectors of the cell causes electrolytic gas generation. This gas generation ceases (the "off" state) if any electrical or ionic pathway is opened (i.e., disconnected) and is reduced if any component in the series circuit develops a high resistance, as current is thereby attenuated (a "partially on" state). By way of the present invention, the "off" state may be achieved by influence of the applied electrolytic current and the differential pressure between the gas electrolytically produced and the combination of environmental pressure communicated to the reference region within the anode endplate and the compression of the resiliently-compressible member. The pressure differential (dP) across the anode current collector may be expressed as:

$$dP = P_e + P_c - P_g$$

wherein $P_e$ is the environmental pressure, $P_c$ is the pressure applied by the resiliently-compressible member, and $P_g$ is the gas pressure in the gas region. When the pressure in the gas region exceeds the combined pressure in the reference region ($P_e + P_c$), the dP value becomes negative, and the anode current collector deflects into the resiliently-compressible member and moves away from the anode support, causing mechanical separation and opening of the electrical circuit. The reestablishment of the "on" state may be part of the normal operation of the self-regulating electrolytic gas generator and is ensured by the judicious selection of the resiliently-compressible member such that the mechanical energy stored therein results in a force upon the active area of the electrolyzer sufficient to restore mechanical contact between the anode current collector and the anode support. Similarly, in a case where the environmental pressure (i.e., the barometric pressure or blood pressure of a subject having a cell implant utilizing the generated gas) changes, there will be a respective change in the displacement of the anode current collector so as to properly regulate the generation of gas and, thereby, adjust the pressure of the gas-treated implant.

While the "on"-"off" function may be suitable for general control of generated gas pressure, it may be preferable to regulate the current to a lower, non-zero value in order to achieve the finest pressure control. A "partially on" condition may be effected when the gas pressure $P_g$ and reference region pressure (sum of the resiliently-compressible member compression $P_c$ and environmental pressure $P_e$) have equalized and current continues to flow at a reduced rate proportional to the steady state rate of gas delivery to the application. Under constant power or voltage control of the electrolytic gas generator, current through the cell is reduced, in this case, by the added series resistance imposed by the longer and/or more tortuous conduction path. Referring to FIG. 8, which shows the "partially on" state, it can be seen that the anode current collector and the anode support are not in complete contact. As a result, current flowing through the cell must take a longer path through the anode support, and there is greater contact resistance due to the smaller area of contact and the reduced contact pressure between the anode current collector and the anode support.

In engineering the self-regulating electrolytic gas generator component properties for a desired current attenuation function in the correct pressure range, the mechanical properties of the resiliently-compressible member and the anode current collector, the contact and sheet resistivity properties of the anode current collector and the anode support, and the amount of compression of the resiliently-compressible member achieved should be taken into account. For the "on" state, where the gas pressure ($P_g$) and the reference region pressure ($P_e + P_c$) produce a zero or positive differential pressure (dP), the endplate cavity depth and resiliently-compressible member thickness should be selected such that the compressed thickness of the resiliently-compressible member, when the endplate is fully compressed against the gaskets in the perimeter seal region, is storing the desired $P_c$.

This may be derived from the compressibility of the resiliently-compressible member, which is preferably selected from within the elastic deformation region of the material's stress-strain property in compression.

Although the electrolytic gas generator of the present invention has been described herein in certain embodiments as comprising, amongst other things, a reversibly distensible anode current collector and a resiliently-compressible member configured to bias the reversibly distensible anode current collector to a flattened state, it is to be understood that, in accordance with the present invention, one could modify such an electrolytic gas generator to instead have a reversibly distensible cathode current collector and a resiliently-compressible member configured to bias the reversibly distensible cathode current collector to a flattened state. Moreover, it is to be understood that, in accordance with the present invention, it may be desirable in certain instances for an electrolytic gas generator to comprise, amongst other things, a reversibly distensible anode current collector, a resiliently-compressible member configured to bias the reversibly distensible anode current collector to a flattened state, a reversibly distensible cathode current collector, and a resiliently-compressible member configured to bias the reversibly distensible cathode current collector to a flattened state.

As can be appreciated, the electrolytic gas generator of the present invention may be incorporated into a multi-cell stack, either made up exclusively of multiple units of the electrolytic gas generator of the present invention or in combination with conventional and/or novel electrolytic gas generators or other electrochemical cells.

The extension of the above-described principles to an all-liquid system—wherein a liquid-phase or dissolved product is delivered to the application by means of diffusion, and the auto-regulation of the electrolysis reaction is achieved in the identical circuit-breaking manner (as governed by increase or decrease in electrolyte volume and, therefore, pressure during the course of electrolysis)—is an additional feature of the self-regulating principle described here.

Figure 9:
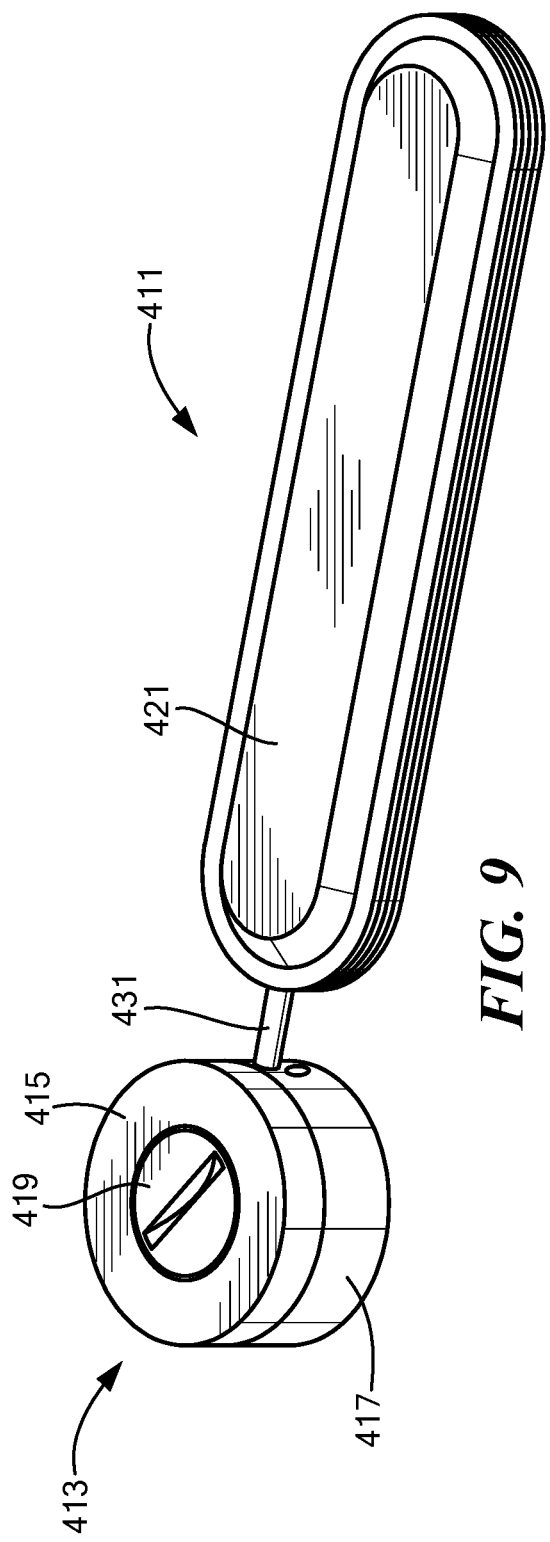
FIG. 9 is a schematic perspective view of a first embodiment of an implant system constructed according to the present invention.

Referring now to FIG. 9, there is shown a first embodiment of an implant system constructed according to the present invention, the implant system being represented generally by reference numeral 411. (For simplicity and clarity, certain components of implant system 411 that are not critical to an understanding of the present invention are either not shown or described herein or are shown and/or described herein in a simplified manner.)

Implant system 411 may comprise an electrolytic gas generator 413. Electrolytic gas generator 413, in turn, may comprise any of the electrolytic gas generators described above encased within a housing top 415 and a housing bottom 417. Electrolytic gas generator 413 may further comprise a battery lid 419 under which the battery (not shown) for powering the electrolytic gas generator may be disposed.

Implant system 411 may further comprise a container 421 for holding implanted cells and/or tissues. Container 421 may be, for example, a conventional container for holding implanted cells and/or tissues or may be, for example, a container of the type disclosed in U.S. Patent Application Publication No. US 2015/0112247 A1.

Implant system 411 may further comprise tubing 431 for fluidically connecting electrolytic gas generator 413 to container 421. More specifically, one end of tubing 431 may be fluidically coupled to the oxygen outlet of electrolytic gas generator 413 and the other end of tubing may be fluidically coupled to the interior of container 421. (Alternatively, tubing 431 could be used to fluidically couple the hydrogen outlet of electrolytic gas generator 413 to the interior of container 421.)

Figure 10:
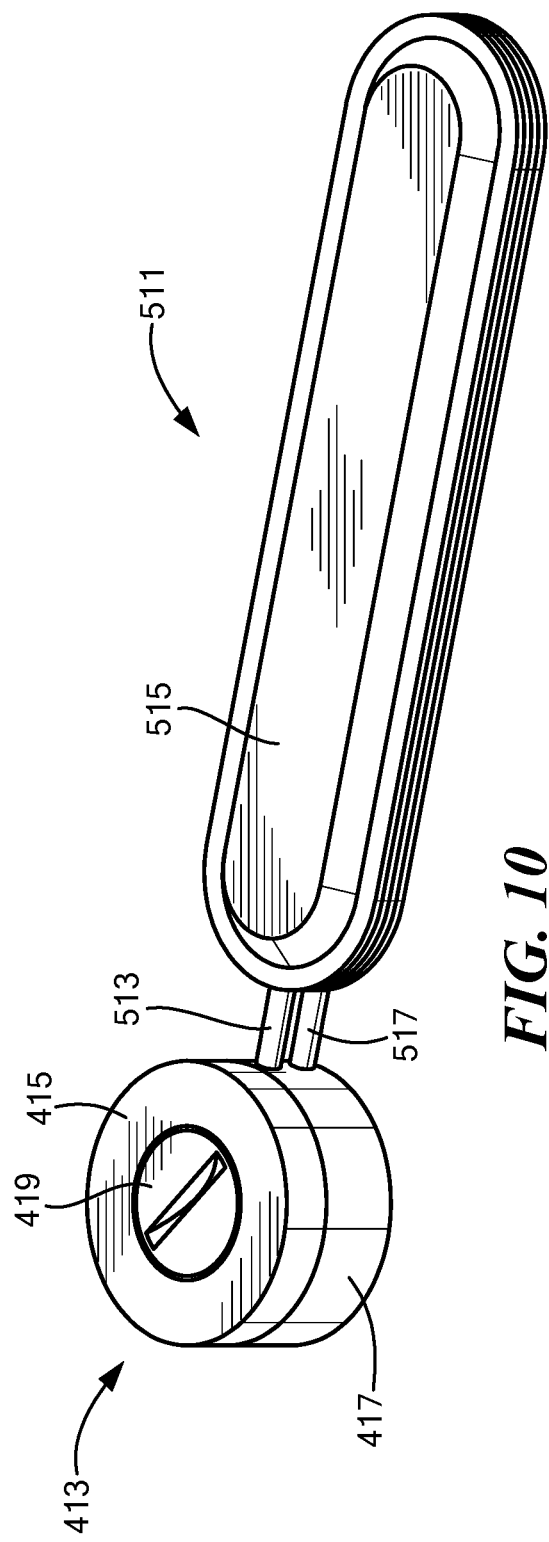
FIG. 10 is a schematic perspective view of a second embodiment of an implant system constructed according to the present invention.

Referring now to FIG. 10, there is shown a second embodiment of an implant system constructed according to the present invention, the implant system being represented generally by reference numeral 511. (For simplicity and clarity, certain components of implant system 511 that are not critical to an understanding of the present invention are either not shown or described herein or are shown and/or described herein in a simplified manner.)

Implant system 511 may be similar in most respects to implant system 411, a principal difference between the two implant systems being that, whereas implant system 411 may comprise tubing 431 for fluidically coupling either the oxygen outlet or the hydrogen outlet of electrolytic gas generator 413 to the interior of container 421, implant system 511 may comprise a first tubing 513 for fluidically coupling the oxygen outlet of electrolytic gas generator 413 to the interior of a container 515 and a second tubing 517 for fluidically coupling the hydrogen outlet of electrolytic gas generator 413 to the interior of container 515. Container 515 may be, for example, a container of the type disclosed in U.S. Patent Application Publication No. US 2015/0112247 A1. Container 515 may optionally include a separate interface to the implanted tissue for diffusion of one or the other electrolytically generated gas away from the implant and into the body, instead of into the cells or tissues encapsulated in container 515.

The following examples are provided for illustrative purposes only and are in no way intended to limit the scope of the present invention:

Example 1

A pre-existing, small electrolysis cell was adapted for use as a self-regulating electrolytic gas generator. The cell used machined poly(etheretherketone) plastic endplates and stainless steel fasteners to maintain a constant mechanical load to the active and seal areas of the cell.

The membrane-electrode assembly (MEA) at the heart of the cell utilized Solvay Aquivion® E79-04SX perfluorosulfonic acid (PFSA) film as the proton-exchange membrane (PEM) and utilized platinum black catalysts (Engelhard, 4 mg/cm$^2$) for the electrocatalysts. The electrocatalysts were blended with Aquivion® PFSA solution (Solvay Specialty Polymers) and applied to the PEM by decal transfer at 1000 psi and 175° C. to unitize the MEA. The anode electrocatalyst contained iridium for improved voltage efficiency.

The circular active catalyst area (2 cm$^2$) of the MEA was electrically contacted and mechanically reinforced on both sides with porous, conductive media comprising supports. The cathode support was porous carbon (Toray TGPH-090), and the anode support was porous titanium (ADMA Products). The border of the MEA was sealed with an adhesive-backed vinyl gasket.

The cathode current collector was a platinum-coated titanium sheet with a tab for edge collection. The anode current collector (diaphragm collector) was a WaMM™ membrane (Giner, Inc., Newton, Mass.) comprising a carbon nanotube/PFSA blend fabricated per Example 8, Build 2, of U.S. Pat. No. 9,595,727 B2. The WaMM™ membrane was selected due to its high selective permeability of water vapor and good electrical conductivity, which are required for good cell performance. The WaMM™ membrane was cut to extend to the outer edge of the seal area and included a tab for current collection. The cylindrical volume defined by the anode face of the MEA, the inside wall of the anode side gasket, and the face of WaMM™ membrane contacting the anode support comprised the internal volume at high relative pressure.

The WaMM™ membrane was supported on the face opposite the anode support by a 1/16" thick, resiliently-compressible, open-cell silicone rubber foam material (density—12 lbs/ft$^3$) cut to the same diameter as the active area. In this section of the assembly, the seal area of the cell comprised a 1/16" thick square-profile, Buna-N rubber O-ring which resided peripherally about the foam. A small hole in the face of the anode side endplate allowed for communication of the region defined by the foam to the outside environment at low relative pressure.

Figure 11:
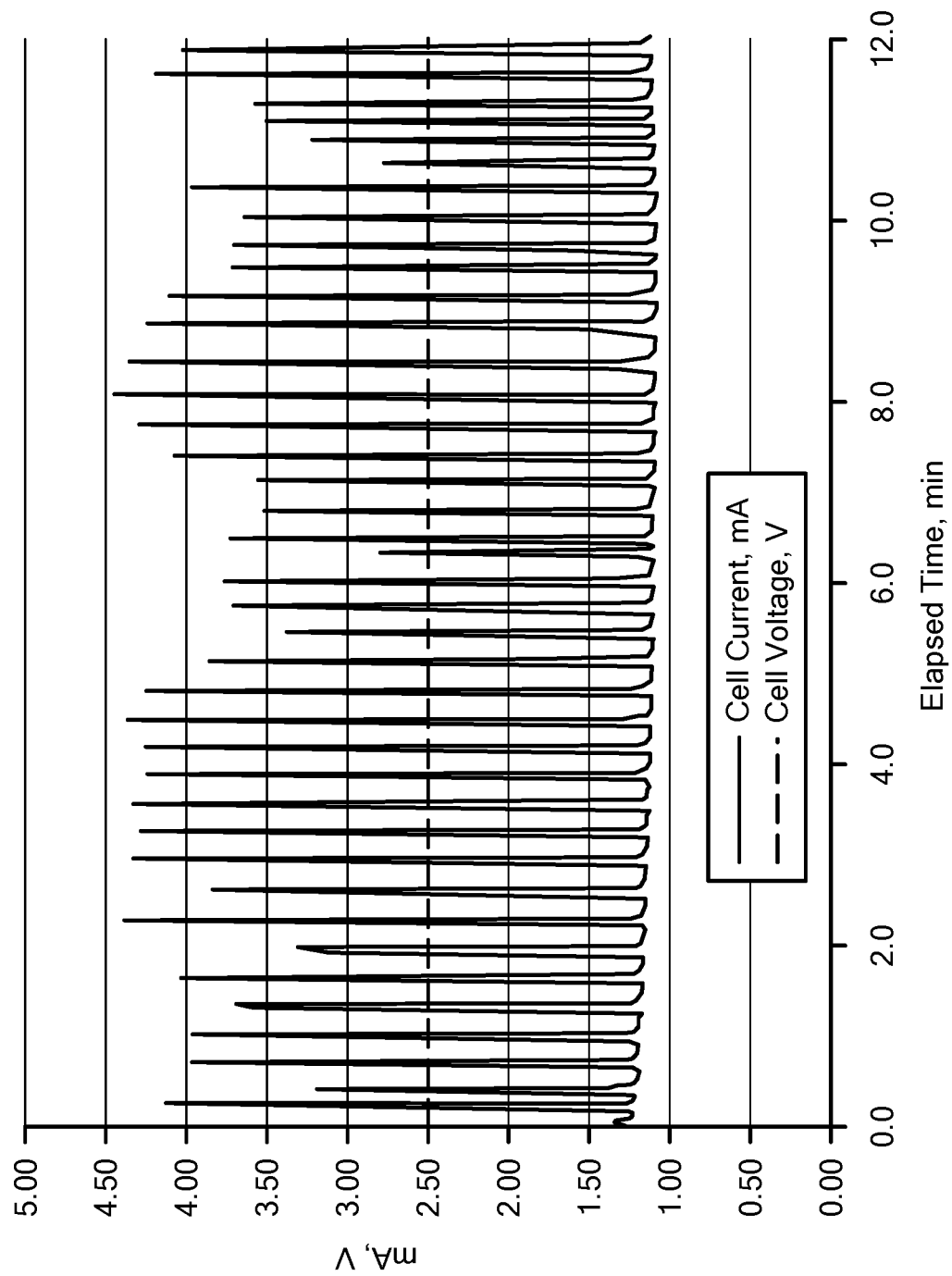
FIG. 11 is a graph depicting current and voltage as a function of time for the electrolytic gas generator described in Example 1.

The application of 2.5 volts from a DC power supply to the cathode and anode collector tabs of this self-regulating electrolytic gas generator caused an immediate increase in cell current to about 8 mA, followed by a steady drop to about 1.5 mA over about 10 minutes. Referring to the chart of FIG. 11, after this steady decrease, the cell was observed to begin oscillating in current indefinitely, with jumps from 1 mA to about 4 mA at approximately 20 second intervals. The rate of gas generation was thus decreasing at gas pressure maxima (approximately 20 psig in this case) and restored after a period of time sufficient for pressure to be relieved by mass transfer from the high relative pressure side of the diaphragm collector to the extent that the degree of electrical contact between the anode support and the diaphragm collector necessary for high current operation could be restored. Restoration of this current allowed renewed pressure differential at constant applied voltage, thereby causing another pressure-current-time cycle.

Example 2

A pre-existing, small electrolysis cell was adapted for use as a self-regulating electrolytic gas generator. The cell used machined poly(etheretherketone) plastic endplates and stainless steel fasteners to maintain a constant mechanical load to the active and seal areas of the cell. Registration pin holes were added to maintain alignment of the gaskets and oxygen port.

The membrane-electrode assembly (MEA) at the heart of the cell utilized Solvay Aquivion® E79-05S perfluorosulfonic acid (PFSA) film as the proton-exchange membrane (PEM) and utilized platinum black catalysts (Engelhard, 4 mg/cm$^2$) for the electrocatalysts. The electrocatalysts were blended with Aquivion® PFSA solution (Solvay Specialty Polymers) and applied to the PEM by decal transfer at 1000 psi and 175° C. to unitize the MEA. The anode electrocatalyst contained iridium for improved voltage efficiency.

The circular active catalyst area (1 cm$^2$) of the MEA was electrically contacted and mechanically reinforced on both sides with porous, conductive media comprising supports. The cathode support was porous carbon (Toray TGPH-090), and the anode support was porous titanium (ADMA Products). The border of the MEA was sealed with polytetrafluoroethylene gaskets on the periphery of both anode and cathode faces.

The cathode current collector was a platinum-coated titanium sheet with a tab for edge collection. The anode current collector was a platinum-coated titanium annulus with a tab for edge collection. Between the MEA and the anode current collector were a non-conductive annulus with a port for gas collection (contacting the MEA) and a conductive diaphragm made of Cho-Seal 1215 elastomer (a conductive material made of silver-plated copper filler in a silicone binder, a product of Parker Chomerics, Woburn, Mass.) which lay between the non-conductive annulus and the anode current collector. The Cho-Seal 1215 was selected due to its good electrical conductivity and elastic mechanical properties. The cylindrical volume defined by the anode face of the MEA, the inside walls of the anode side gasket and non-conductive port, and the face of the conductive diaphragm contacting the anode support comprised the internal volume at high relative pressure.

The conductive diaphragm was supported on the face opposite the anode support by a 1/8" thick, open-cell polyurethane polyether foam material (Formulation 1034 fabricated by New England Foam Products, LLC, Hartford, Conn.; density—0.9 lb/ft$^3$) cut to a diameter slightly larger than the active area diameter. In this section of the assembly, the seal area of the cell comprised a 0.07" thick, square-profile, polytetrafluoroethylene gasket which resided peripherally about the foam. A small hole in the center of the anode side endplate face allowed for communication of the region defined by the foam to the outside environment at low relative pressure. A second hole through the face of the anode side endplate allowed for gas generated at the MEA and collected through the non-conductive port to be routed out of the cell.

Figure 12:
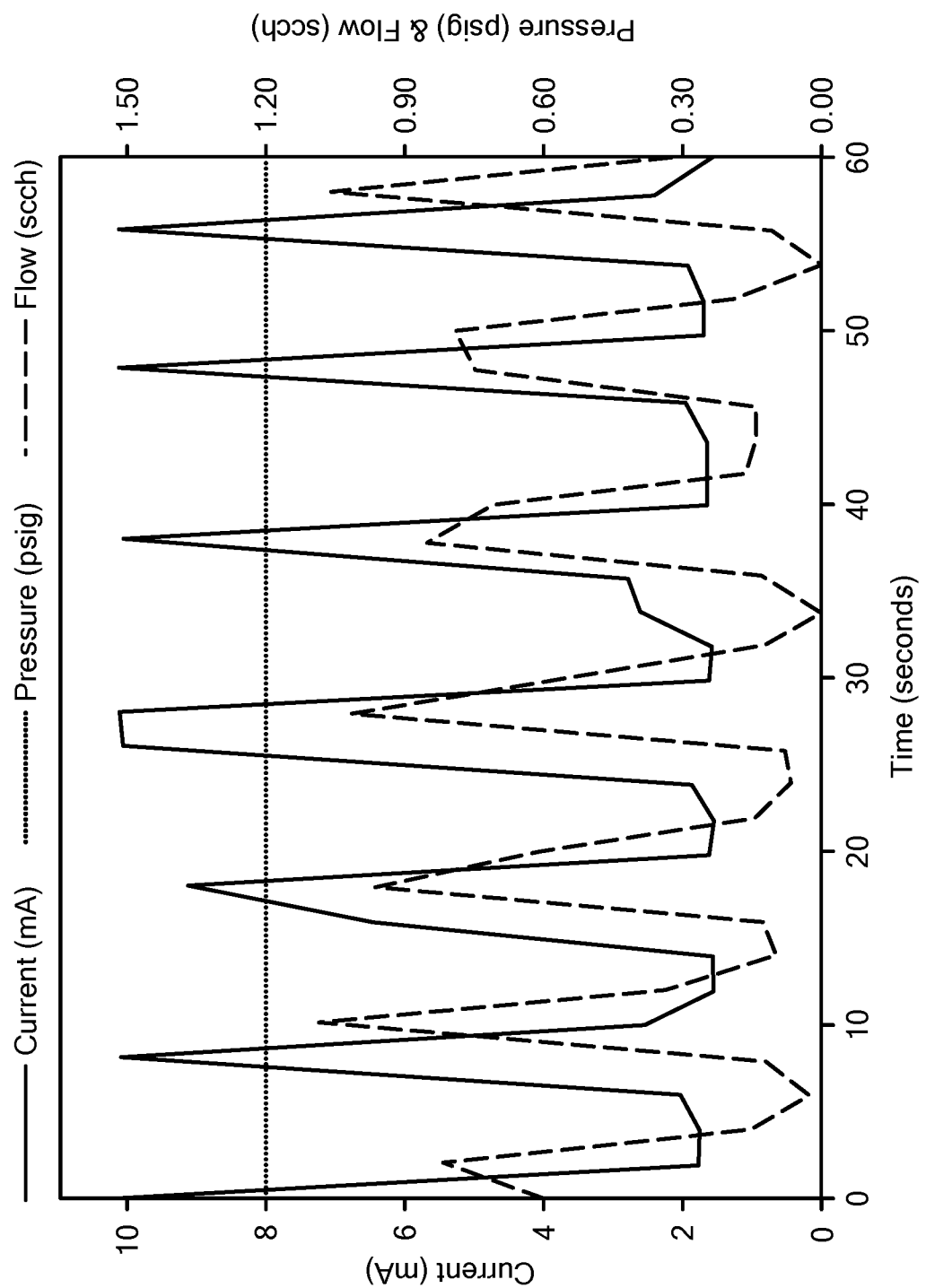
FIG. 12 is a graph depicting current, pressure, and oxygen flow rate as a function of time for the electrolytic gas generator described in Example 2.

The electrolytic gas generator so described was fitted to a test system having a DC power supply to provide current to the cell, a flowmeter (Alicat Scientific M-0.5SCCM-D) and a pressure transducer (IFM PX3238) on the oxygen outlet, and flow restricting valve venting to the atmosphere. Application of more than 1.5 VDC from a DC power supply between the cathode and anode collector tabs of this self-regulating electrolytic gas generator caused an immediate increase in cell current to about 10 mA, followed by current oscillation, where the lower limit slowly decreased from 4 mA to 2 mA as the pressure in the cell rose. Referring to FIG. 12, after this steady decrease in the lower limit, the cell was observed to begin oscillating in current indefinitely between about 2 mA to about 10 mA at approximately 10 second intervals. The rate of gas generation (oxygen gas flow rate in standard cubic centimeters per hour, scch) was also oscillating in accordance with the self-regulation of the cell current and a constant regulated gas pressure of about 1.2 psig was observed between the outlet of the cell and the flow restricting valve.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. An electrolytic gas generator for electrolyzing a reactant to generate at least a first gas, the electrolytic gas generator comprising:
    (a) a polymer electrolyte membrane, the polymer electrolyte membrane having opposing first and second faces;
    (b) a first electrode, the first electrode being electrically coupled to the first face of the polymer electrolyte membrane;
    (c) a second electrode, the second electrode being electrically coupled to the second face of the polymer electrolyte membrane;
    (d) a first current collector, the first current collector comprising an electrically-conductive diaphragm and being reversibly deformable between a first state in which the first current collector is electrically coupled to the first electrode and a second state in which the first current collector is at least partially electrically disconnected from the first electrode;
(e) a second current collector, the second current collector being electrically-conductive and being electrically coupled to the second electrode; and
(f) a power source, the power source being electrically coupled to the first current collector and to the second current collector;
(g) whereby, when the first current collector is in the first state and the reactant is supplied to the electrolytic gas generator, a first gas is generated at the interface of the first electrode and the polymer electrolyte membrane.

2. The electrolytic gas generator as claimed in claim 1 wherein the electrolytic gas generator is a water electrolyzer.

3. The electrolytic gas generator as claimed in claim 1 wherein the first current collector is in direct physical and electrical contact with the first electrode in the first state and is completely physically and electrically disconnected from the first electrode in the second state.

4. The electrolytic gas generator as claimed in claim 1 wherein the first current collector is in direct physical and electrical contact with the first electrode in the first state and is partially physically and electrically disconnected from the first electrode in the second state.

5. The electrolytic gas generator as claimed in claim 1 wherein the first electrode is an anode and wherein the second electrode is a cathode.

6. The electrolytic gas generator as claimed in claim 1 further comprising a resiliently-compressible member engaged with the first current collector to bias the first current collector towards the first state.

7. The electrolytic gas generator as claimed in claim 6 wherein the resiliently-compressible member comprises a block of foam.

8. The electrolytic gas generator as claimed in claim 7 wherein the foam is open-cell foam.

9. The electrolytic gas generator as claimed in claim 7 wherein the foam is closed-cell foam.

10. The electrolytic gas generator as claimed in claim 1 wherein the first current collector is elastic.

11. The electrolytic gas generator as claimed in claim 1 wherein the electrically-conductive diaphragm is non-porous.

12. The electrolytic gas generator as claimed in claim 11 wherein the electrically-conductive diaphragm is gas-permeable.

13. The electrolytic gas generator as claimed in claim 1 wherein the second current collector comprises at least one pore.

14. The electrolytic gas generator as claimed in claim 1 further comprising a first fluid inlet for admitting outside fluid into the electrolytic gas generator to be electrolyzed.

15. The electrolytic gas generator as claimed in claim 1 further comprising a first fluid outlet for discharging from the electrolytic gas generator a first gas generated thereby.

16. The electrolytic gas generator as claimed in claim 1 wherein the electrically-conductive diaphragm comprises a polymer.

17. The electrolytic gas generator as claimed in claim 1 wherein the electrically-conductive diaphragm is non-porous and comprises one of a silicone film with electrically-conductive particles dispersed therein and a silicone sheet with electrically-conductive particles dispersed therein.

18. The electrolytic gas generator as claimed in claim 1 wherein the electrically-conductive diaphragm is non-porous and comprises a solid polymer electrolyte into which electrically-conductive materials are dispersed.

19. An implant system comprising:
(a) the electrolytic gas generator of claim 1;
(b) a container for holding implantable one or more cells and/or tissues; and
(c) a first tubing for conducting the first gas generated by the electrolytic gas generator to the container.

20. An electrolytic gas generator for electrolyzing a reactant to generate at least a first gas, the electrolytic gas generator comprising:
(a) a polymer electrolyte membrane, the polymer electrolyte membrane having opposing first and second faces;
(b) a first electrode, the first electrode being electrically coupled to the first face of the polymer electrolyte membrane;
(c) a second electrode, the second electrode being electrically coupled to the second face of the polymer electrolyte membrane;
(d) a first current collector, the first current collector being electrically-conductive and being reversibly deformable between a first state in which the first current collector is electrically coupled to the first electrode and a second state in which the first current collector is at least partially electrically disconnected from the first electrode, wherein the first current collector comprises a non-porous, gas-impermeable, electrically-conductive diaphragm;
(e) a second current collector, the second current collector being electrically-conductive and being electrically coupled to the second electrode; and
(f) a power source, the power source being electrically coupled to the first current collector and to the second current collector;
(g) whereby, when the first current collector is in the first state and the reactant is supplied to the electrolytic gas generator, a first gas is generated at the interface of the first electrode and the polymer electrolyte membrane.

21. An electrolytic gas generator for electrolyzing a reactant to generate at least a first gas, the electrolytic gas generator comprising:
(a) a polymer electrolyte membrane, the polymer electrolyte membrane having opposing first and second faces;
(b) a first electrode, the first electrode being electrically coupled to the first face of the polymer electrolyte membrane;
(c) a second electrode, the second electrode being electrically coupled to the second face of the polymer electrolyte membrane;
(d) a first current collector, the first current collector being electrically-conductive and being reversibly deformable between a first state in which the first current collector is electrically coupled to the first electrode and a second state in which the first current collector is at least partially electrically disconnected from the first electrode, wherein the first current collector comprises an electrically-conductive diaphragm and a ring terminal;
(e) a second current collector, the second current collector being electrically-conductive and being electrically coupled to the second electrode; and
(f) a power source, the power source being electrically coupled to the first current collector and to the second current collector;
(g) whereby, when the first current collector is in the first state and the reactant is supplied to the electrolytic gas generator, a first gas is generated at the interface of the first electrode and the polymer electrolyte membrane.

22. An electrolytic gas generator for electrolyzing water to generate oxygen and hydrogen gases, the electrolytic gas generator comprising:
 (a) a polymer electrolyte membrane, the polymer electrolyte membrane having opposing first and second faces;
 (b) a first electrode, the first electrode being electrically coupled to the first face of the polymer electrolyte membrane;
 (c) a second electrode, the second electrode being electrically coupled to the second face of the polymer electrolyte membrane;
 (d) a first current collector, the first current collector comprising an electrically-conductive diaphragm and being reversibly deformable, when subjected to gas pressure, between a first state in which the first current collector is electrically coupled to the first electrode and a second state in which the first current collector is at least partially electrically disconnected from the first electrode;
 (e) a second current collector, the second current collector being electrically-conductive and being electrically coupled to the second electrode;
 (f) a first seal, the first seal being disposed around a periphery of the first electrode, the first seal comprising a fluid outlet for discharging one of hydrogen and oxygen generated at the first electrode;
 (g) a second seal, the second seal being disposed around a periphery of the second electrode, the second seal comprising a fluid outlet for discharging the other of hydrogen and oxygen generated at the second electrode;
 (h) a first endplate, the first current collector being positioned between the first endplate and the polymer electrolyte membrane;
 (i) a second endplate, the second current collector being positioned between the second endplate and the polymer electrolyte membrane;
 (j) wherein at least one of the first seal, the second seal, the first endplate and the second endplate has at least one inlet for admitting outside water; and
 (k) a power source, the power source being electrically coupled to the first current collector and to the second current collector;
 (l) whereby, when the first current collector is in the first state and water is supplied to the electrolytic gas generator, one of hydrogen and oxygen gas is generated at the interface of the first electrode and the polymer electrolyte membrane and the other of hydrogen and oxygen is generated at the interface of the second electrode and the polymer electrolyte membrane.

23. The electrolytic gas generator as claimed in claim 22 wherein the first current collector is in direct physical and electrical contact with the first electrode in the first state and is completely physically and electrically disconnected from the first electrode in the second state.

24. The electrolytic gas generator as claimed in claim 22 wherein the first current collector is in direct physical and electrical contact with the first electrode in the first state and is partially physically and electrically disconnected from the first electrode in the second state.

25. The electrolytic gas generator as claimed in claim 22 wherein the first electrode is an anode and wherein the second electrode is a cathode.

26. The electrolytic gas generator as claimed in claim 22 further comprising a resiliently-compressible member positioned between and engaged with the first endplate and the first current collector to bias the first current collector towards the first state.

27. The electrolytic gas generator as claimed in claim 26 wherein the resiliently-compressible member comprises a block of foam.

28. The electrolytic gas generator as claimed in claim 27 wherein the electrically-conductive diaphragm is elastic and non-porous, wherein the foam is open-cell foam, and wherein the first endplate comprises at least one pore.

29. The electrolytic gas generator as claimed in claim 28 further comprising an ultrafiltration membrane positioned within the at least one pore of the first endplate.

30. The electrolytic gas generator as claimed in claim 22 wherein the second current collector comprises at least one pore and wherein the second endplate comprises at least one pore.

31. The electrolytic gas generator as claimed in claim 30 further comprising a liquid-permeable, gas-impermeable interface layer positioned between the second current collector and the second endplate.

32. The electrolytic gas generator as claimed in claim 22 wherein at least one of the first seal and the second seal has a fluid inlet for admitting outside water.

33. The electrolytic gas generator as claimed in claim 22 wherein the electrically-conductive diaphragm is non-porous.

34. The electrolytic gas generator as claimed in claim 22 wherein the electrically-conductive diaphragm is non-porous and comprises one of a silicone film with electrically-conductive particles dispersed therein and a silicone sheet with electrically-conductive particles dispersed therein.

35. The electrolytic gas generator as claimed in claim 22 wherein the electrically-conductive diaphragm is non-porous and comprises a solid polymer electrolyte into which electrically-conductive materials are dispersed.

36. An implant system comprising:
 (a) the electrolytic gas generator of claim 22;
 (b) a container for holding implantable one or more cells and/or tissues; and
 (c) a first tubing for conducting one of hydrogen and oxygen generated by the electrolytic gas generator to the container; and
 (d) a second tubing for conducting the other of hydrogen and oxygen generated by the electrolytic gas generator to the container.

37. An electrolytic gas generator for electrolyzing water to generate oxygen and hydrogen gases, the electrolytic gas generator comprising:
 (a) a polymer electrolyte membrane, the polymer electrolyte membrane having opposing first and second faces;
 (b) a first electrode, the first electrode being electrically coupled to the first face of the polymer electrolyte membrane;
 (c) a second electrode, the second electrode being electrically coupled to the second face of the polymer electrolyte membrane;
 (d) a first current collector, the first current collector being electrically-conductive and being reversibly deformable, when subjected to gas pressure, between a first state in which the first current collector is electrically coupled to the first electrode and a second state in which the first current collector is at least partially electrically disconnected from the first electrode, wherein the first current collector comprises an elastic, non-porous, gas-impermeable, electrically-conductive diaphragm;

(e) a second current collector, the second current collector being electrically-conductive and being electrically coupled to the second electrode;
(f) a first seal, the first seal being disposed around a periphery of the first electrode, the first seal comprising a fluid outlet for discharging one of hydrogen and oxygen generated at the first electrode;
(g) a second seal, the second seal being disposed around a periphery of the second electrode, the second seal comprising a fluid outlet for discharging the other of hydrogen and oxygen generated at the second electrode;
(h) a first endplate, the first current collector being positioned between the first endplate and the polymer electrolyte membrane;
(i) a resiliently-compressible member positioned between and engaged with the first endplate and the first current collector to bias the first current collector towards the first state, wherein the resiliently-compressible member comprises a block of foam;
(j) a second endplate, the second current collector being positioned between the second endplate and the polymer electrolyte membrane;
(k) wherein at least one of the first seal, the second seal, the first endplate and the second endplate has at least one inlet for admitting outside water; and
(l) a power source, the power source being electrically coupled to the first current collector and to the second current collector;
(m) whereby, when the first current collector is in the first state and water is supplied to the electrolytic gas generator, one of hydrogen and oxygen gas is generated at the interface of the first electrode and the polymer electrolyte membrane and the other of hydrogen and oxygen is generated at the interface of the second electrode and the polymer electrolyte membrane.

* * * * *